(12) United States Patent
Chang et al.

(10) Patent No.: US 10,722,571 B2
(45) Date of Patent: Jul. 28, 2020

(54) RABIES VIRUS G PROTEIN EPITOPE, AND RABIES VIRUS NEUTRALISING BINDING MOLECULE THAT BINDS SPECIFICALLY THERETO

(71) Applicant: CELLTRION INC., Incheon (KR)

(72) Inventors: Shin Jae Chang, Incheon (KR); Soo Young Lee, Incheon (KR); Pan Kyeom Kim, Incheon (KR); Jung Sun Ahn, Incheon (KR); Min Joo Choo, Incheon (KR)

(73) Assignee: Celltrion Inc., Incheon (KR)

( * ) Notice: Subject to any disclaimer, the term of this patent is extended or adjusted under 35 U.S.C. 154(b) by 0 days.

(21) Appl. No.: 15/735,068

(22) PCT Filed: Jun. 9, 2016

(86) PCT No.: PCT/KR2016/006145
§ 371 (c)(1),
(2) Date: Dec. 8, 2017

(87) PCT Pub. No.: WO2016/200189
PCT Pub. Date: Dec. 15, 2016

(65) Prior Publication Data
US 2019/0022211 A1    Jan. 24, 2019

(30) Foreign Application Priority Data

Jun. 10, 2015    (KR) .................. 10-2015-0082284

(51) Int. Cl.
*A61K 39/42*     (2006.01)
*G01N 33/53*     (2006.01)
(Continued)

(52) U.S. Cl.
CPC ............ *A61K 39/205* (2013.01); *A61P 31/14* (2018.01); *C07K 14/005* (2013.01); *C07K 16/10* (2013.01);
(Continued)

(58) Field of Classification Search
None
See application file for complete search history.

(56) References Cited

U.S. PATENT DOCUMENTS

2008/0102523 A1    5/2008    Kim et al.

FOREIGN PATENT DOCUMENTS

| IN | 201617019965 A | 8/2016 |
|---|---|---|
| KR | 10-1076602 B1 | 10/2011 |

(Continued)

OTHER PUBLICATIONS

Rudikoff et al., "Single amino acid substitution altering antigen-binding specificity," Proc Natl Acad Sci USA 79:1979-1983 (Year: 1982).*

(Continued)

*Primary Examiner* — M Franco G Salvoza
(74) *Attorney, Agent, or Firm* — John P. White; Cooper and Dunham LLP

(57) ABSTRACT

This invention relates to a rabies virus G protein epitope and a rabies-virus-neutralizing binding molecule that binds specifically thereto, wherein different epitope sites of rabies virus G protein are identified and binding molecules that bind thereto and a cocktail thereof can be found to retain neutralizing activity against various rabies viruses.

15 Claims, 1 Drawing Sheet

Specification includes a Sequence Listing.

(51) Int. Cl.
- *A61K 39/205* (2006.01)
- *C07K 16/10* (2006.01)
- *C07K 14/005* (2006.01)
- *A61P 31/14* (2006.01)
- *A61K 39/00* (2006.01)

(52) U.S. Cl.
CPC .. *A61K 2039/505* (2013.01); *A61K 2039/507* (2013.01); *A61K 2039/521* (2013.01); *C07K 2317/34* (2013.01); *C07K 2317/76* (2013.01); *C07K 2317/92* (2013.01); *C12N 2760/20122* (2013.01)

(56) References Cited

FOREIGN PATENT DOCUMENTS

| KR | 10-1739313 B1 | 5/2017 | | |
|----|---------------|--------|----|----|
| WO | WO 2005/023849 A2 | 3/2005 | | |
| WO | WO-2015088256 A1 | * | 6/2015 | ............. C07K 16/10 |

OTHER PUBLICATIONS

WIPO English translation of WO-2015088256-A1 (Year: 2019).*
Rupprecht et al., "Current status and development of Vaccines and Other Biologics for Human Rabies Prevention," Expert Review of Vaccines, vol. 15, No. 6: 731-749 (Year: 2016).*
Bakker et al., "Novel human monoclonal antibody combination effectively neutralizing natural rabies virus variants and individual in vitro escape mutants," J. Virol., 79(14): 9062-8 (Year: 2005).*
International Search Report dated Sep. 7, 2016 in connection with PCT International Application No. PCT/KR2016/006145.
Lina Sun et al., "Generation and characterization of neutralizing human recombinant antibodies against antigenic site II of rabies virus glycoprotein", *Appl Microbiol Biotechnol*, 2012.
WHO Consultation on a Rabies Minoclonal Antibody Cocktail for Rabies Post Exposure Treatment, WHO, Geneva, May 23-24, 2002.
Elvin A. Kabat et al., "Sequences of Proteins of Immunological Interest", (5th), National Institutes of Health, Bethesda, MD, 1991.
Cheryl Paes et al., "Atomic-Level Mapping of Antibody Epitopes on a GPCR", *J. Am. Chem. Soc.*, 2009.
Monique Lafon et al., "Antigenic Sites on the CVS Rabies Virus Glycoprotein: Analysis with Monoclonal Antibodies", *J. Gen. Virol.*, 1983.
Wilfred E. Marissen et al., "Novel Rabies Virus-Neutralizing Epitope Recognized by Human Monoclonal Antibody: Fine Mapping and Escape Mutant Analysis", *Journal of Virology*, 2005.

* cited by examiner

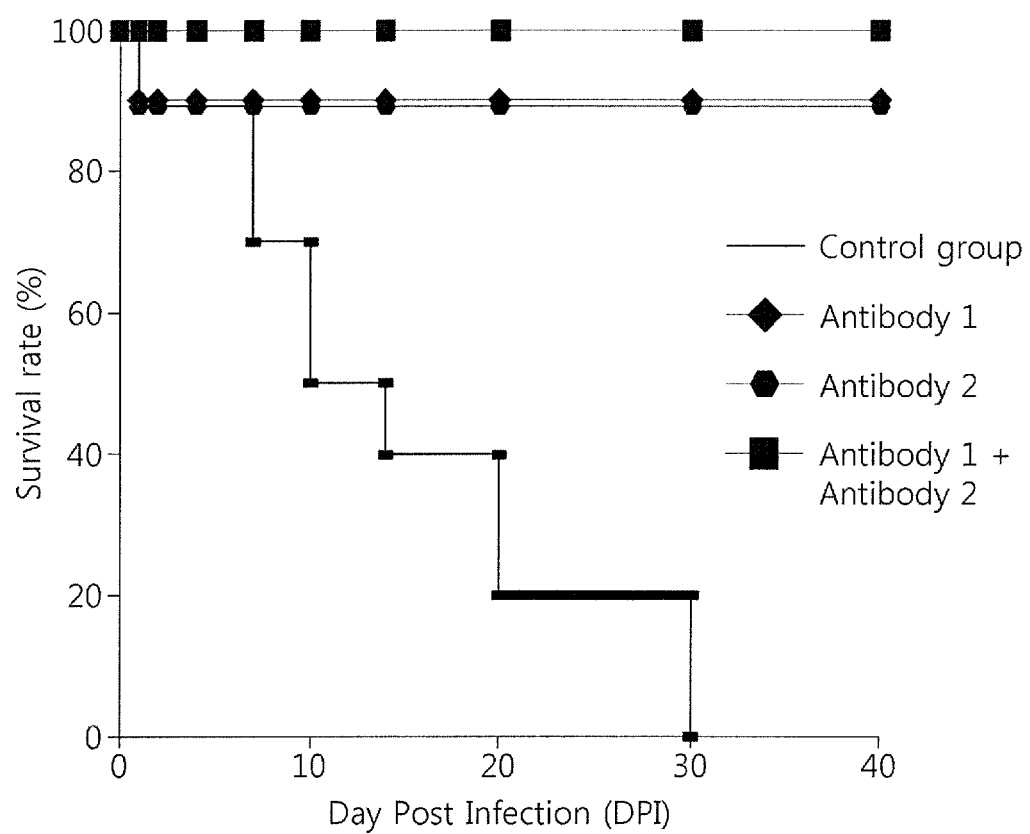

RABIES VIRUS G PROTEIN EPITOPE, AND RABIES VIRUS NEUTRALISING BINDING MOLECULE THAT BINDS SPECIFICALLY THERETO

CROSS-REFERENCE TO RELATED APPLICATIONS

This application is a § 371 national stage of PCT International Application No. PCT/KR2016/006145, filed Jun. 9, 2016, claiming priority of Korean Patent Application No. KR 10-2015-0082284, filed Jun. 10, 2015, the contents of each of which are hereby incorporated by reference into the application.

REFERENCE TO A SEQUENCE LISTING

This application incorporates by reference nucleotide and/or amino acid sequences which are present in the file named "171208_90222_Substitute_Sequence_Listing_CAE.txt", which is 38.5 kilobytes in size, and which was created Dec. 8, 2017 in the IBM-PC machine format, having an operating system compatibility with MS-Windows, which is contained in the text file filed Dec. 8, 2017 as part of this application.

TECHNICAL FIELD

The present invention relates to a rabies virus G protein (glycoprotein) epitope and a rabies-virus-neutralizing binding molecule that binds specifically thereto.

BACKGROUND ART

Rabies is a viral zoonosis, and affects mainly wild animals and companion animals as well as mammals including humans, and thus causes acute brain diseases. Rabies is a fatal disease that entails the risk of death through a single infection, and is known to be the disease having the highest mortality rate with AIDS. Such rabies is spread all over the world, with more than 10 million people being treated after infection every year, with 40,000 to 70,000 deaths each year.

Rabies is transmitted through saliva and blood, and is usually caused by being bitten by rabies-infected dogs or cats. It may also be carried by most mammals, including skunks, bats, and the like.

The rabies virus exhibits actual onset symptoms after reaching the cranial nerves through the terminal nerve tissue of the body. The human brain originally contains a blood brain barrier that blocks the invasion of external substances, so that viruses cannot penetrate. However, the rabies virus infects the central nervous system of the brain by passing through the blood brain barrier via RVG protein (rabies virus glycoprotein).

In addition to symptoms similar to colds at the beginning of rabies, itching or fever is felt in the bite area. As rabies progresses, there may occur neurological abnormalities, such as anxiety, hydrophobia (swallowing of liquids such as water causes spasm of the muscles and severe pain to thus incur fear of water), fear of wind (wind makes the sensory organs more sensitive), excitement, paralysis, mental disorder, etc. It also causes hypersensitivity to sunlight. After 2 to 7 days of observation of these symptoms, the nerves and muscles of the entire body are paralyzed, inducing a coma, resulting in respiratory failure leading to death.

Treatment after exposure to rabies includes an injury by biting (post-exposure prophylaxis). An injury by biting includes administration of the antibody for passive immunization and immediate topical wound protection (anti-rabies immunoglobulin: hereinafter, referred to as "anti-rabies antibody"), and administration of the vaccine for active immunization. The currently developed anti-rabies antibody includes human-derived rabies immunoglobulin (hereinafter, referred to as "HRIG") and equine-derived rabies immunoglobulin (hereinafter, referred to as "ERIG"). HRIG is not efficiently supplied, is expensive, and is a polyclonal antibody, and thus has low efficacy per unit weight. Furthermore, HRIG is derived from the human blood and has a high risk of potential infection of human-derived disease such as HIV. On the other hand, ERIG is inexpensive but exhibits low therapeutic efficiency compared to HRIG, and is thus administered in a much higher dose to patients. However, ERIG is an antibody derived from horses, different from humans, and may thus cause anaphylaxis. Accordingly, in order to overcome the inefficient supply and problems with the polyclonal antibody, the use of a monoclonal antibody that is able to neutralize the rabies virus has been proposed. In the 1980s, a rabies-virus-neutralizing mouse monoclonal antibody was developed (Schumacher C L et al., J. Clin. Invest. Vol. 84, p. 971-975, 1989), but the direct administration thereof to human patients is limited owing to defects such as a short half-life in the human body, the absence of an antibody-mediated immune response, induction of HAMA (human anti-mouse antibody), and the like.

Moreover, the WHO has presented several recommendations to replace existing HRIG or ERIG (WHO Consultation on a Rabies Monoclonal Antibody Cocktail for Rabies Post-Exposure Treatment. WHO, Geneva, 23-24 May 2002). Among these, it has been proposed that in order for the monoclonal antibody to serve as a therapeutic agent for rabies, two or three antibodies should be cocktailed and bound to different sites of the rabies virus surface glycoprotein.

Therefore, for effective rabies treatment, there is an urgent need to develop a human monoclonal antibody and an antibody cocktail against any rabies virus, which are not derived from the blood to thus have high safety against potential infection, enable mass production through incubation, and are composed exclusively of antibodies having efficacy to thus ensure uniform quality and exhibit high efficiency per unit dose.

DISCLOSURE

Technical Problem

In order to solve the problems as above, the present inventors demonstrated that the epitope of the human antibody (Korean Patent Application No. 10-2014-0178030) that binds to the rabies virus to thus have neutralizing activity is located at amino acid positions 33, 34, 35, 38, 200, 202 and 215 of the rabies virus G protein (SEQ ID NO:2) or at amino acid positions 331 and 333 thereof, and also that the neutralizing activity of the antibody cocktail comprising two kinds of antibodies binding to different epitopes is determined.

Accordingly, the present invention is intended to provide a rabies-virus-neutralizing binding molecule that binds to an epitope located between $33^{rd}$ to $333^{rd}$ amino acid residues of a wild-type rabies virus G protein represented by SEQ ID NO:2.

In addition, the present invention is intended to provide an immunoconjugate, configured such that at least one tag is additionally coupled to the binding molecule.

In addition, the present invention is intended to provide a nucleic acid molecule encoding the binding molecule.

In addition, the present invention is intended to provide an expression vector into which the nucleic acid molecule is inserted.

In addition, the present invention is intended to provide a cell line, configured such that a host cell is transformed with the expression vector so as to produce a binding molecule that binds to the rabies virus and has neutralizing activity.

In addition, the present invention is intended to provide a medicinal composition for the diagnosis, prevention or treatment of rabies, comprising the binding molecule.

In addition, the present invention is intended to provide a kit for the diagnosis, prevention or treatment of rabies, comprising the binding molecule.

In addition, the present invention is intended to provide a method of diagnosing, preventing or treating rabies using the binding molecule.

In addition, the present invention is intended to provide a method of producing the binding molecule by incubating the cell line.

In addition, the present invention is intended to provide a method of detecting the rabies virus using the binding molecule.

In addition, the present invention is intended to provide a medicinal composition for the prevention or treatment of rabies, comprising a) a first binding molecule that binds to an epitope located between $33^{rd}$ to $215^{th}$ amino acid residues of a wild-type rabies virus G protein represented by SEQ ID NO:2; and b) a second binding molecule that binds to an epitope located between $331^{st}$ to $333^{rd}$ amino acid residues of a wild-type rabies virus G protein represented by SEQ ID NO:2.

In addition, the present invention is intended to provide a method of diagnosing, preventing or treating rabies, comprising a) administering the above composition in a therapeutically effective amount to a subject; b) simultaneously administering the first binding molecule and the second binding molecule in therapeutically effective amounts to a subject; or c) sequentially administering the first binding molecule and the second binding molecule in therapeutically effective amounts to a subject.

In addition, the present invention is intended to provide a polypeptide, comprising an epitope located between $33^{rd}$ to $215^{th}$ amino acid residues of a wild-type rabies virus G protein represented by SEQ ID NO:2.

In addition, the present invention is intended to provide a polypeptide, comprising an epitope located between $331^{st}$ to $333^{rd}$ amino acid residues of a wild-type rabies virus G protein represented by SEQ ID NO:2.

In addition, the present invention is intended to provide a method of screening a rabies-virus-neutralizing binding molecule that binds specifically to the polypeptide.

In addition, the present invention is intended to provide a rabies virus vaccine composition comprising the polypeptide.

Technical Solution

Therefore, an embodiment of the present invention provides a rabies-virus-neutralizing binding molecule that binds to an epitope located between $33^{rd}$ to $333^{rd}$ amino acid residues of a wild-type rabies virus G protein represented by SEQ ID NO:2.

In an embodiment of the present invention, the epitope may be an epitope located between $33^{rd}$ to $215^{th}$ amino acid residues of the wild-type rabies virus G protein represented by SEQ ID NO:2, and more particularly, may be an epitope comprising at least one selected from the group consisting of $33^{rd}$, $34^{th}$, $35^{th}$, $38^{th}$, $200^{th}$, $202^{nd}$ and $215^{th}$ amino acid residues thereof.

In an embodiment of the present invention, the rabies-virus-neutralizing binding molecule that binds to the above epitope may have a binding affinity (KD) of less than $1 \times 10^{-8}$ M. In another embodiment, the binding molecule may have a binding affinity of less than $5 \times 10^{-9}$ M. In still another embodiment, the binding molecule may have a binding affinity of less than $1 \times 10^{-9}$ M. In yet another embodiment, the binding molecule may have a binding affinity of less than $5 \times 10^{-10}$ M. In still yet another embodiment, the binding molecule may have a binding affinity of less than $1 \times 10^{-10}$ M. In a further embodiment, the binding molecule may have a binding affinity of less than $5 \times 10^{-11}$ M. In still a further embodiment, the binding molecule may have a binding affinity of less than $1 \times 10^{-11}$ M. In yet a further embodiment, the binding molecule may have a binding affinity of less than $5 \times 10^{-12}$ M. In still yet a further embodiment, the binding molecule may have a binding affinity of less than $1 \times 10^{-12}$ M.

In an embodiment of the present invention, the rabies-virus-neutralizing binding molecule that binds to the above epitope may be a binding molecule comprising a) a variable domain comprising a CDR1 of SEQ ID NO:3, a CDR2 of SEQ ID NO:4, and a CDR3 of SEQ ID NO:5; and/or b) a variable domain comprising a CDR1 of SEQ ID NO:6, a CDR2 of SEQ ID NO:7, and a CDR3 of SEQ ID NO:8.

In another embodiment, the binding molecule may be a binding molecule comprising a variable domain of SEQ ID NO:15 and/or a variable domain of SEQ ID NO:16. In still another embodiment, the binding molecule may be a binding molecule comprising a heavy chain of SEQ ID NO:19 and/or a light chain of SEQ ID NO:20.

In another embodiment of the present invention, the epitope may be an epitope located between $331^{st}$ to $333^{rd}$ amino acid residues of the wild-type rabies virus G protein represented by SEQ ID NO:2, and more particularly, may be an epitope comprising at least one selected from the group consisting of $331^{st}$ and $333^{rd}$ amino acid residues thereof.

In an embodiment of the present invention, the rabies-virus-neutralizing binding molecule that binds to the above epitope may have a binding affinity ($K_D$) of less than $1 \times 10^{-9}$ M. In another embodiment, the binding molecule may have a binding affinity of less than $3 \times 10^{-10}$ M. In still another embodiment, the binding molecule may have a binding affinity of less than $1 \times 10^{-10}$ M. In yet another embodiment, the binding molecule may have a binding affinity of less than $3 \times 10^{-11}$ M. In still yet another embodiment, the binding molecule may have a binding affinity of less than $1 \times 10^{-11}$ M. In a further embodiment, the binding molecule may have a binding affinity of less than $3 \times 10^{-12}$ M. In still a further embodiment, the binding molecule may have a binding affinity of less than $1 \times 10^{-12}$ M. In yet a further embodiment, the binding molecule may have a binding affinity of less than $3 \times 10^{-13}$ M. In still yet a further embodiment, the binding molecule may have a binding affinity of less than $1 \times 10^{-13}$ M.

The binding affinity ($K_D$) may be measured using surface plasmon resonance, for example, a BIACORE system.

In an embodiment of the present invention, the rabies-virus-neutralizing binding molecule that binds to the above epitope may be a binding molecule comprising a) a variable domain comprising a CDR1 of SEQ ID NO:9, a CDR2 of SEQ ID NO:10, and a CDR3 of SEQ ID NO:11; and/or b)

a variable domain comprising a CDR1 of SEQ ID NO:12, a CDR2 of SEQ ID NO:13, and a CDR3 of SEQ ID NO:14.

In another embodiment, the binding molecule may be a binding molecule comprising a variable domain of SEQ ID NO: 17 and/or a variable domain of SEQ ID NO: 18. In still another embodiment, the binding molecule may be a binding molecule comprising a heavy chain of SEQ ID NO:21 and/or a light chain of SEQ ID NO:22.

Meanwhile, in the present invention, CDR of the variable domain is determined through a typical method using a system devised by Kabat et al. (Kabat et al., Sequences of Proteins of Immunological Interest (5$^{th}$), National Institutes of Health, Bethesda, Md. (1991)). Although the determination of CDR used in the present invention is performed using the Kabat method, a binding molecule comprising CDR determined by other methods, such as an IMGT method, a Chothia method, an AbM method, and the like, falls within the scope of the present invention.

In an embodiment of the present invention, the binding molecule may be an antibody or a fragment thereof. The binding molecule may be, but is not limited to, Fab, Fv, a diabody, a chimeric antibody, a humanized antibody or a human antibody. An embodiment of the present invention provides a fully human antibody that binds to the rabies virus. As used herein, the term "antibody" is used to have as broad a meaning as possible, and particularly includes an intact monoclonal antibody, a polyclonal antibody, a multi-specific antibody formed from two or more intact antibodies (e.g. a bispecific antibody), and an antibody fragment that shows the desired biological activity. The antibody is a protein that is produced by an immune system capable of recognizing a specific antigen and binding thereto. The antibody is typically configured to have a Y-shaped protein comprising four amino acid chains (two heavy chains and two light chains). Each antibody has two domains including a variable domain and a constant domain. The variable domain, which is located at the ends of the arms of Y, binds to the target antigen and interacts therewith. The variable domain includes a complementarity-determining region (CDR) that recognizes the specific binding site on the specific antigen and binds thereto. The constant domain, which is located at the tail of Y, is recognized by the immune system and interacts therewith. The target antigen has a plurality of binding sites called epitopes, recognized by CDRs on antibodies. Respective antibodies specifically binding to different epitopes have different structures. Therefore, a single antigen may have at least one antibody corresponding thereto.

Furthermore, the present invention includes a functional variant of the antibody. Such antibody variants are regarded as functional variants of the inventive antibody so long as they are capable of competing with the inventive antibody in order to specifically bind to the rabies virus or to a G protein thereof. Such functional variants include, but are not limited to, derivatives the primary conformational sequences of which are substantially similar, and examples thereof include in-vitro or in-vivo modifications, chemicals and/or biochemicals, and they are not found in the parent monoclonal antibody of the present invention. Examples of such modifications may include acetylation, acylation, covalent bonding of nucleotides or nucleotide derivatives, covalent bonding of lipids or lipid derivatives, crosslinking, disulfide bonding, glycosylation, hydroxylation, methylation, oxidation, pegylation, proteolysis and phosphorylation. The functional variant may be selectively an antibody comprising an amino acid sequence resulting from subjecting at least one amino acid to substitution, insertion, deletion or combinations thereof, compared to the amino acid sequence of the parent antibody. Furthermore, the functional variant may include the truncated form of the amino acid sequence in one or both of an amino terminus and a carboxyl terminus. The functional variant of the present invention may have binding affinity the same as or different from, i.e. higher or lower than, that of the parent antibody of the present invention, but may still bind to the rabies virus or to a G protein thereof. For example, the amino acid sequence of the variable domain, including, but not limited to, a framework structure or a hypervariable domain, especially CDR3, may be modified. Typically, a light- or heavy-chain domain includes three hypervariable domains having three CDRs and more conserved domains, namely a framework region (FR). The hypervariable domain includes an amino acid residue from CDR and an amino acid residue from a hypervariable loop. The functional variant, which falls within the scope of the present invention, may have an amino acid sequence homology of about 50%~99%, about 60%~99%, about 80%~99%, about 90%~99%, about 95%~99%, or about 97%~99% with the parent antibody of the invention. In order to optimally arrange amino acid sequences to be compared and also in order to define similar or identical amino acid residues, among computer algorithms, Gap or Best-fit, known to those skilled in the art, may be used. The functional variant may be obtained by subjecting the parent antibody or a portion thereof to a known molecular biological process including PCR or mutagenesis/partial mutagenesis using an oligomer nucleotide, or to an organic synthesis process, but the present invention is not limited thereto.

Meanwhile, the rabies virus may be derived from any one individual selected from the group consisting of dog, cow, mongoose, bat, skunk, raccoon, coyote, fox, and wolf, without being limited thereto.

In addition, the present invention provides an immuno-conjugate configured such that at least one tag is further coupled to the binding molecule. For example, a drug may be additionally attached to the antibody according to the present invention. The antibody according to the present invention may be used in the form of an antibody-drug conjugate including the drug. When the antibody-drug conjugate (ADC), that is, the immunoconjugate, is used to topically deliver the drug, targeted delivery of the drug moiety to infected cells becomes possible. When the drug agent is administered without being conjugated, unacceptable levels of toxicity to normal cells may be caused. By increasing not only the drug conjugation and the drug releasability but also selectivity of the polyclonal antibody and monoclonal antibody (mAb), maximum efficacy and minimum toxicity of ADC may be obtained.

The use of typical means for attaching the drug moiety to the antibody, for example, through covalent bonding, may cause the production of heterogeneous molecular mixtures in which the drug moiety is attached to many sites of the antibody. For example, a cytotoxic drug is conjugated to the antibody through many lysine residues of the antibody to thus produce a heterogeneous antibody-drug conjugate mixture. Depending on the reaction conditions, such a heterogeneous mixture typically has a distribution whereby a number of antibodies attached to the drug moiety ranges from 0 to at least about 8. Furthermore, each subgroup of the conjugate comprising the drug moiety and the antibody at a specific integer ratio is a potential heterogeneous mixture in which the drug moiety is attached to various sites of the antibody. The antibody is a biomolecule that is large, complicated and structurally various, and often has many reactive functional groups. The reactivity of a linker reagent and a drug-linker intermediate is dependent on factors such as pH, concentration, salt concentration, and cosolvent.

In addition, the present invention provides a nucleic acid molecule encoding the binding molecule. For instance, the present invention includes an isolated nucleic acid molecule encoding the rabies-virus-neutralizing binding molecule that binds to the epitope of the wild-type rabies virus G protein.

The nucleic acid molecule includes any nucleic acid molecule in which the amino acid sequence of the antibody of the present invention is translated into a polynucleotide sequence as known to those skilled in the art. Thus, various polynucleotide sequences may be prepared using ORF (Open Reading Frame), and may also be incorporated in the nucleic acid molecule of the present invention.

In addition, the present invention provides an expression vector into which the nucleic acid molecule is inserted.

In an embodiment of the present invention, the expression vector may include, but is not limited to, any one selected from the group consisting of an expression vector available from Celltrion, such as a MarEx vector (Korean Patent No. 10-1076602), and a commercially widely useful pCDNA vector, F, R1, RP1, Col, pBR322, ToL, and Ti vector; a cosmid; phages, such as lambda, lambdoid, M13, Mu, pi P22, Qp, T-even, T2, T3, T7, etc.; and plant viruses, and any expression vector known to those skilled in the art may be used in the present invention, and the expression vector may be selected depending on the properties of the host cell of interest. The introduction of the vector into the host cell may be performed through calcium phosphate transfection, viral infection, DEAE-dextran-mediated transfection, lipofectamine transfection, or electroporation, but the present invention is not limited thereto, and those skilled in the art may adopt an introduction process suitable for the expression vector and the host cell. The expression vector preferably contains at least one selection marker, but is not limited thereto, and selection is possible depending on whether or not the product is capable of being obtained using the vector containing no selection marker. Choosing the selection marker depends on the host cell of interest, and is performed using any process known to those skilled in the art, and thus the present invention is not limited in connection therewith.

In order to easily purify the binding molecule of the present invention, a tag sequence may be inserted into the expression vector and thus fused. The tag may include, but is not limited to, a hexa-histidine tag, a hemagglutinin tag, a myc tag or a flag tag, and any tag may be useful in the present invention so long as it facilitates purification as known to those skilled in the art.

In addition, the present invention provides a cell line, configured such that a host cell is transformed with the expression vector so as to produce the binding molecule that binds to the rabies virus and thus has neutralizing activity.

In addition, the present invention provides a method of producing a binding molecule binding to the rabies virus and having neutralizing activity, comprising a) incubating the cell line; and b) recovering the expressed binding molecule.

In an embodiment of the present invention, the cell line may include, but is not limited to, mammals, plants, insects, fungi, or cells of cellular origin. Any one selected from the group consisting of mammalian cells, such as CHO cells, F2N cells, CSO cells, BHK cells, Bowes melanoma cells, HeLa cells, 911 cells, AT1080 cells, A549 cells, HEK 293 cells and HEK293T cells may be used as the host cell, but the present invention is not limited thereto, and any cells may be used so long as they are useful as host cell for mammals, as known to those skilled in the art.

In addition, the present invention provides a medicinal composition for the diagnosis, prevention or treatment of rabies, comprising the binding molecule.

The medicinal composition for the prevention or treatment according to the present invention may include a pharmaceutically acceptable excipient, in addition to the binding molecule having rabies-virus-neutralizing activity. Pharmaceutically acceptable excipients are well known to those skilled in the art.

Furthermore, the medicinal composition for the prevention or treatment according to the present invention may include at least one other rabies therapeutic agent, and may also include a variety of monoclonal antibodies, thereby exhibiting synergistic neutralizing activity.

Moreover, the medicinal composition for the prevention or treatment according to the present invention may further include at least one other therapeutic agent or diagnostic agent. The therapeutic agent may include, but is not limited to, an anti-virus drug. Such a drug may be an antibody, a small molecule, an organic or inorganic compound, an enzyme, a polynucleotide sequence, an anti-viral peptide, and the like.

The medicinal composition for the prevention or treatment according to the present invention is aseptic and stable under production and storage conditions, and may be provided in the form of a powder so as to be reconstructed into an appropriate pharmaceutically acceptable excipient during or before delivery. A sterile powder for the preparation of a sterile injection solution is preferably obtained through vacuum drying and lyophilization to produce an active ingredient powder and additional desired ingredients from the pre-sterilized-filtered solution thereof. The medicinal composition of the present invention may be in a solution phase, and may include an appropriate pharmaceutically acceptable excipient that is added and/or mixed before or during the delivery to provide a unit dosage administration form. Preferably, the pharmaceutically acceptable excipient used in the present invention is adequate for drug concentration and is able to maintain suitable flowability, and the absorption thereof may be delayed as necessary.

The optimal route selection for the administration of the medicinal composition for the prevention or treatment according to the present invention is affected by various factors, including physical-chemical properties of active molecules in the medicinal composition, the urgency of the clinical circumstances and the relationship of the plasma concentration of the active molecule to the desired therapeutic effect. For example, the monoclonal antibody of the present invention may be prepared together with a carrier for preventing rapid release, such as a controlled release formulation, including an implant and a microcapsule delivery system. In the present invention, a biodegradable and biocompatible polymer, such as ethylene vinyl acetate, polyanhydride, polyglycolic acid, collagen, polyorthoester and polylactic acid, may be used. Furthermore, the monoclonal antibody may be coated with or administered with a substance or compound for preventing the inactivation of the antibody. For example, the monoclonal antibody may be administered together with a suitable carrier-liposome or diluent.

A method of administering the medicinal composition for the prevention or treatment according to the present invention may include oral administration and parenteral administration, and for example, the administration route may be intravenous administration, but is not limited thereto.

The oral formulation may be provided in the form of tablets, troches, medicinal drops, aqueous or oily suspensions, powders or dispersion granules, emulsions, rigid capsules, soft gelatin capsules, syrups or elixirs, pills, sugar-coated tablets, liquids, gels or slurry. Such a formulation may include, but is not limited to, a pharmaceutically acceptable excipient containing an inert diluent, a granulating or disintegrating agent, a binder, a lubricant, a preservative, a colorant, a flavor, a sweetening agent, vegetable or mineral oils, a wetting agent and a thickener.

The parenteral formulation may be provided in the form of an aqueous or non-aqueous isotonic sterile non-toxic injection or in the form of injection solutions or suspensions. The solutions or suspensions may include oils, fatty acids, local anesthetic agents, preservatives, buffers, viscosity- or solubility-increasing agents, water-soluble antioxidants, oil-soluble antioxidants and metal-chelating agents, as well as medicaments such as 1,3-butanediol, a Ringer's solution, a Hank's solution, and an isotonic sodium chloride solution, which are non-toxic to a receptor at applied doses and concentrations.

The administered amount of the medicinal composition for the prevention or treatment according to the present invention present invention depends on the treatment subject, severity of disease or status, administration rate and doctor's prescription. Useful as the active ingredient, the binding molecule may be administered once or divided into multiple administrations several times per day in a dose of 0.001 to 10 mg/kg (body weight) or 0.005 to 1 mg/kg (body weight) to a mammal through parenteral routes. In some cases, a dose smaller than the aforementioned range may be more suitable, and a larger dose may be applied without causing harmful side effects and may be distributed in small amounts several times in one day.

It is preferred that the binding molecule of the present invention used in the medicinal composition for the diagnosis be detectably labeled. Various methods that may be used to label biomolecules are well known to those skilled in the art and are considered to fall within the scope of the present invention. Examples of the label useful in the present invention may include enzymes, radioactive isotopes, colloidal metals, fluorescent compounds, chemiluminescent compounds and bioluminescent compounds. Commonly used labels include fluorescent substances (e.g., fluorescein, rhodamine, Texas red, etc.), enzymes (such as horseradish peroxidase, β-galactosidase, alkaline phosphatase), radioactive isotopes (e.g. 32P or 125I), biotin, digoxigenin, colloidal metals, chemiluminescent or bioluminescent compounds (such as dioxetane, luminol or acridinium). Labeling methods such as covalent bonding, iodination, phosphorylation, biotinylation, etc. of enzymes or biotinyl groups are well known in the art. Detection methods include, but are not limited to, autoradiography, fluorescence microscopy, direct and indirect enzyme reactions, and the like. A commonly used detection assay is the radioisotope or non-radioisotope method. Particularly useful are western blotting, overlay analysis, RIA (Radioimmuno Assay) and IRMA (ImmuneRadioimmunometric Assay), EIA (Enzyme Immuno Assay), ELISA (Enzyme Linked Immuno Sorbent Assay), FIA (Fluorescent Immuno Assay) and CLIA (Chemiluminescent Immune Assay).

In addition, the present invention provides a kit for the diagnosis, prevention or treatment of rabies, comprising a) the binding molecule; and b) a vessel.

In the kit for the diagnosis, prevention or treatment according to the present invention, a solid carrier may be included in b) the vessel. The binding molecule of the present invention may be attached to the solid carrier, and the solid carrier may be porous or non-porous, or may be planar or non-planar.

In addition, the present invention provides a method of diagnosing rabies, comprising bringing a subject sample into contact with the binding molecule; and b) analyzing the results of step a) to determine infection with rabies.

In the diagnosis method of the present invention, the sample may be, but is not limited to, any one selected from the group consisting of sputum, spit, blood, sweat, lung cells, mucus of lung tissue, respiratory tissue and saliva of a subject, and the sample may be prepared using a process typically known to those skilled in the art.

In addition, the present invention provides a method of preventing or treating rabies, comprising administering the binding molecule in a therapeutically effective amount to a subject.

For example, when people travel to areas in which rabies is known to be present, the human monoclonal antibody of the present invention may be administered thereto, thereby imparting immunity against rabies virus within 1 day, 2 days, 3 days or several days.

In addition, the present invention provides a method of detecting the rabies virus, comprising a) bringing a subject sample into contact with the binding molecule; and b) measuring whether the binding molecule binds specifically to the subject sample.

In the rabies virus detection method of the present invention, the subject sample may include, but is not limited to, blood, serum, saliva, sputum, spit, sweat, tissue or other biological materials from the (potentially) infected subject, and may be prepared through a typical process known to those skilled in the art. The (potentially) infected subject may be a human, but may include animals that are suspected to be carriers of the rabies virus. The subject sample may first be manipulated to make it more appropriate for the detection method. Preferably, the binding molecule or immunoconjugate of the present invention is brought into contact with the subject sample under conditions that permit the formation of an immunological complex between the binding molecule and the rabies virus or its antigenic component present in the subject sample. The formation of the immunological complex that shows the presence of the rabies virus in the subject sample is detected and measured through appropriate means. To this end, immunoassays such as radioimmunoassay (RIA), ELISA, immunofluorescence, immunohistochemistry, FACS, BIACORE, and western blot analysis may be performed, but the present invention is not limited thereto.

In addition, the present invention provides a medicinal composition (hereinafter, referred to as a "cocktail composition") for the diagnosis, prevention or treatment of rabies, comprising a) a first binding molecule that binds to an epitope located between $33^{rd}$ to $215^{th}$ amino acid residues of a wild-type rabies virus G protein represented by SEQ ID NO:2; and b) a second binding molecule that binds to an epitope located between $331^{st}$ to $333^{rd}$ amino acid residues of a wild-type rabies virus G protein represented by SEQ ID NO:2.

In an embodiment of the present invention, the cocktail composition may comprise a) the first binding molecule and b) the second binding molecule at a concentration ratio of 1:9~9:1.

In an embodiment of the present invention, the epitope to which the first binding molecule binds may include at least one selected from the group consisting of $33^{rd}$, $34^{th}$, $35^{th}$, 38th, 200th, 202nd and 215th amino acid residues of the wild-type rabies virus G protein represented by SEQ ID NO:2.

In an embodiment of the present invention, the epitope to which the second binding molecule binds may include at least one selected from the group consisting of 331st and 333rd amino acid residues of the wild-type rabies virus G protein represented by SEQ ID NO:2.

In an embodiment of the present invention, the first binding molecule may have a binding affinity (KD) of less than $1\times10^{-8}$ M. In another embodiment, the binding molecule may have a binding affinity of less than $5\times10^{-9}$ M. In still another embodiment, the binding molecule may have a binding affinity of less than $1\times10^{-9}$ M. In yet another embodiment, the binding molecule may have a binding affinity of less than $5\times10^{-10}$ M. In still yet another embodiment, the binding molecule may have a binding affinity of less than $1\times10^{-10}$ M. In a further embodiment, the binding molecule may have a binding affinity of less than $5\times10^{-11}$ M. In still a further embodiment, the binding molecule may have a binding affinity of less than $1\times10^{-11}$ M. In yet a further embodiment, the binding molecule may have a binding affinity of less than $5\times10^{-12}$ M. In still yet a further embodiment, the binding molecule may have a binding affinity of less than $1\times10^{-12}$ M.

In an embodiment of the present invention, the second binding molecule may have a binding affinity ($K_D$) of less than $1\times10^{-9}$ M. In another embodiment, the binding molecule may have a binding affinity of less than $3\times10^{-10}$ M. In still another embodiment, the binding molecule may have a binding affinity of less than $1\times10^{-10}$ M. In yet another embodiment, the binding molecule may have a binding affinity of less than $3\times10^{-11}$ M. In still yet another embodiment, the binding molecule may have a binding affinity of less than $1\times10^{-11}$ M. In a further embodiment, the binding molecule may have a binding affinity of less than $3\times10^{-12}$ M. In still a further embodiment, the binding molecule may have a binding affinity of less than $1\times10^{-12}$ M. In yet a further embodiment, the binding molecule may have a binding affinity of less than $3\times10^{-13}$ M. In still yet a further embodiment, the binding molecule may have a binding affinity of less than $1\times10^{-13}$ M.

In an embodiment of the present invention, the first binding molecule may be a binding molecule comprising a) a variable domain comprising a CDR1 of SEQ ID NO:3, a CDR2 of SEQ ID NO:4, and a CDR3 of SEQ ID NO:5; and/or b) a variable domain comprising a CDR1 of SEQ ID NO:6, a CDR2 of SEQ ID NO:7, and a CDR3 of SEQ ID NO:8. In another embodiment, the first binding molecule may be a binding molecule comprising a variable domain of SEQ ID NO:15 and/or a variable domain of SEQ ID NO:16. In still another embodiment, the first binding molecule may be a binding molecule comprising a heavy chain of SEQ ID NO: 19 and/or a light chain of SEQ ID NO:20.

In an embodiment of the present invention, the second binding molecule may be a binding molecule comprising a) a variable domain comprising a CDR1 of SEQ ID NO:9, a CDR2 of SEQ ID NO: 10, and a CDR3 of SEQ ID NO: 11; and/or b) a variable domain comprising a CDR1 of SEQ ID NO:12, a CDR2 of SEQ ID NO:13, and a CDR3 of SEQ ID NO:14. In another embodiment, the second binding molecule may be a binding molecule comprising a variable domain of SEQ ID NO:17 and/or a variable domain of SEQ ID NO: 18. In still another embodiment, the second binding molecule may be a binding molecule comprising a heavy chain of SEQ ID NO:21 and/or a light chain of SEQ ID NO:22.

In an embodiment of the present invention, the binding molecule may be an antibody or an antigen-binding fragment, and an anti-viral drug may be further attached to the antibody.

In an embodiment of the present invention, the cocktail composition may be provided in the form of a sterile injection solution, a lyophilized formulation, a pre-filled injection solution, an oral formulation, an external preparation or a suppository.

In addition, the present invention provides a method of diagnosing, preventing or treating rabies, comprising a) administering the cocktail composition in a therapeutically effective amount to a subject; b) simultaneously administering the first binding molecule and the second binding molecule in therapeutically effective amounts to a subject; or c) sequentially administering the first binding molecule and the second binding molecule in therapeutically effective amounts to a subject.

In the prevention or treatment method of the present invention, a therapeutic agent known to those skilled in the art may be administered therewith. In the prevention or treatment method of the present invention, the administration method may include oral administration and parenteral administration, and the administration route may be, for example, intravenous administration, but is not limited thereto.

In the prevention or treatment method of the present invention, administering an anti-viral drug may be further performed. The anti-viral drug may be, but is not limited to, an anti-rabies virus monoclonal antibody, an anti-rabies virus polyclonal antibody, a DNA polymerase inhibitor, a siRNA formulation or a therapeutic vaccine.

In addition, the present invention provides a method of diagnosing, preventing or treating rabies, comprising a) simultaneously administering the first binding molecule and the second binding molecule in therapeutically effective amounts to a subject; b) sequentially administering the first binding molecule in a therapeutically effective amount and then the second binding molecule in a therapeutically effective amount to a subject; or c) sequentially administering the second binding molecule in a therapeutically effective amount and then the first binding molecule in a therapeutically effective amount to a subject.

In addition, the present invention provides a medicinal composition for the diagnosis, prevention or treatment of rabies, comprising a) simultaneously administering the first binding molecule and the second binding molecule in therapeutically effective amounts to a subject; b) sequentially administering the first binding molecule in a therapeutically effective amount and then the second binding molecule in a therapeutically effective amount to a subject; or c) sequentially administering the second binding molecule in a therapeutically effective amount and then the first binding molecule in a therapeutically effective amount to a subject.

In addition, the present invention provides a kit for the diagnosis, prevention or treatment of rabies, comprising (1) the above medicinal composition comprising the first binding molecule and the second binding molecule in therapeutically effective amounts; and (2) a package insert indicated to represent a) simultaneously administering the first binding molecule and the second binding molecule in therapeutically effective amounts to a subject, b) sequentially administering the first binding molecule in a therapeutically effective amount and then the second binding molecule in a therapeutically effective amount to a subject, or c) sequentially administering the second binding molecule in a therapeutically effective amount and then the first binding molecule in a therapeutically effective amount to a subject.

In addition, the present invention provides a polypeptide, comprising an epitope located between $33^{rd}$ to $215^{th}$ amino acid residues of a wild-type rabies virus G protein represented by SEQ ID NO:2.

The epitope may include at least one selected from the group consisting of $33^{rd}$, $34^{th}$, $35^{th}$, $38^{th}$, $200^{th}$, $202^{rd}$ and $215^{th}$ amino acid residues of the wild-type rabies virus G protein.

In addition, the present invention provides a polypeptide, comprising an epitope located between $331^{st}$ to $333^{rd}$ amino acid residues of a wild-type rabies virus G protein represented by SEQ ID NO:2.

The epitope may include at least one selected from the group consisting of $331^{st}$ and $333^{rd}$ amino acid residues of the wild-type rabies virus G protein.

In the polypeptide of the present invention, the epitope may be used in the form of being linked with a carrier in order to maintain a three-dimensional structure thereof or to ensure efficiency thereof upon use for a vaccine composition or the like. In the present invention, any carrier may be used so long as it is biocompatible and is suitable for realizing the effects of the present invention, and may be selected from among, but is not limited to, a peptide, serum albumin, immunoglobulin, hemocyanin, and polysaccharide.

In addition, the present invention provides a polynucleotide encoding the epitope. The polynucleotide encoding the epitope comprising the above amino acid positions according to the present invention may be used alone in the form of a gene vaccine. Here, the polynucleotide may be used alone without any vector, and may be embedded in a viral or non-viral vector and then transferred into the body. The viral or non-viral vector may be used without limitation so long as it is known to be typically useful in the art to which the present invention belongs. Particularly, examples of the viral vector may include an adenovirus, an adeno-associated virus, a lentivirus, a retrovirus, etc., and the non-viral vector may include a cationic polymer, a nonionic polymer, a liposome, a lipid, a phospholipid, a hydrophilic polymer, a hydrophobic polymer, and at least one combination selected from among them, but the present invention is not limited thereto.

In addition, the present invention provides an expression vector containing the polynucleotide encoding the epitope.

In addition, the present invention provides a recombinant microorganism or virus, which is transformed with the expression vector. In an embodiment, the recombinant microorganism or virus may be recombinant E. coli, recombinant yeast, or a recombinant bacteriophage.

In an embodiment of the present invention, the present invention provides a method of expressing, on the surface of a microorganism or virus, the epitope located between $33^{rd}$ to $215^{th}$ amino acid residues of the wild-type rabies virus G protein represented by SEQ ID NO:2 or the epitope located between $331^{st}$ to $333^{rd}$ amino acid residues of the wild-type rabies virus G protein represented by SEQ ID NO:2. Here, a recombinant vector comprising a sequence encoding an inducible promoter or signal protein and any microorganism or virus containing the recombinant vector may be used. In particular, the appropriate microorganism or virus may include, but is not limited to, recombinant E. coli, recombinant yeast, or a recombinant bacteriophage. In order to express the epitope comprising the above amino acid positions on the surface of the microorganism or virus, a display technique well-known in the art to which the present invention belongs may be utilized. In particular, the expression method of the invention may be performed in a manner in which a polynucleotide sequence encoding the epitope comprising the above amino acid positions may bind to the sequence encoding a promoter or signal protein that induces expression on the surface of microorganism cells or viruses, or in which some of the genetic sites encoding proteins that are originally expressed on the surface may be deleted and then a polynucleotide sequence encoding the epitope comprising the above amino acid positions may be inserted therein, but the present invention is not limited thereto. When using the expression method of the invention, the epitope comprising the above amino acid positions expressed on the surface of the microorganism or virus may be isolated and purified and may thus be applied to certain purposes of the present invention, and moreover, it is possible to selectively obtain an antibody that binds specifically to the epitope comprising the above amino acid positions in the state of being expressed on the surface.

In addition, the present invention provides a method of producing the epitope, comprising incubating the recombinant microorganism or virus.

In addition, the present invention provides a composition for the detection of the rabies virus, comprising the above epitope or a polynucleotide encoding such an epitope.

In addition, the present invention provides a method of screening a rabies-virus-neutralizing binding molecule that binds specifically to the above polypeptide, comprising bringing the binding molecule into contact with the polypeptide.

In an embodiment of the present invention, the binding molecule may be an antibody or an antigen-binding fragment.

The screening method according to the present invention may be performed by any immunoassay method, for example, ELISA, tissue or cell (transfected cell) staining, neutralization assay or other methods known in the art in order to verify desired specificity or functionality, but the present invention is not limited thereto.

In addition, the present invention provides a rabies virus vaccine composition comprising the above polynucleotide.

The vaccine composition of the present invention may further include a pharmaceutically acceptable adjuvant. The adjuvant functions to increase the formation of an antibody when injected into the body, and any adjuvant may be used so long as it is able to achieve the effects of the present invention, and examples thereof may include, but are not limited to, an aluminum salt ($Al(OH)_3$, $AlPO_4$), squalene, sorbitan, polysorbate 80, CpG, liposome, cholesterol, MPL (monophosphoryl lipid A), and GLA (glucopyranosyl lipid A).

The terms used in the present invention are defined as follows.

As used herein, the term "binding molecule" refers to an intact immunoglobulin including monoclonal antibodies, such as chimeric, humanized or human monoclonal antibodies, or to an antigen-binding immunoglobulin, for example, a variable domain, which comprises an immunoglobulin fragment that competes with the intact immunoglobulin in order to bind to the rabies virus, to a G protein (glycoprotein) outside the virus, or to a fragment thereof. Regardless of the structure, an antigen-binding fragment binds with the same antigen that is recognized by the intact immunoglobulin. The antigen-binding fragment may comprise a peptide or polypeptide comprising an amino acid sequence consisting of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of the binding molecule.

As used herein, the term "antigen-binding fragment" indicates Fab, F(ab'), F(ab')$_2$, Fv, dAb, Fd, complementarity-determining region (CDR) fragments, single-chain antibodies (scFv), bivalent single-chain antibodies, single-chain phage antibodies, diabodies, triabodies, tetrabodies, polypeptides that contain at least one fragment of an immunoglobulin that is sufficient to confer specific antigen binding to the polypeptide, etc. The above fragments may be produced synthetically or by enzymatic or chemical cleavage of intact immunoglobulins, or they may be genetically engineered by recombinant DNA techniques. Such production methods are well known in the art.

As used herein, the term "epitope" refers to an antigenic determinant corresponding to a portion of an antigen recognized by the antibody, and indicates a peptide material containing a single peptide or multiple peptides as used in the present specification and claims, and the epitope has the amino acid sequence data represented by SEQ ID NO:2 set forth herein and variants thereof and also includes peptides having active profiles described in the present specification and claims. Thus, even a protein that shows almost the same activity or changed activity should be understood in this sense. Such variants may be intentionally obtained through site-directed mutagenesis, or alternatively, may be accidentally obtained by mutation of a complex or a host that is the producer of the designated subunit thereof. As a method of forming and examining a peptide variant comprising an epitope including a variant, site-directed mutagenesis and random mutagenesis are well known to those skilled in the art.

As used herein, the term "pharmaceutically acceptable excipient" means any inert substance that is combined with an active molecule such as a drug, agent, or binding molecule for preparing an agreeable or convenient dosage form. The pharmaceutically acceptable excipient is an excipient that is non-toxic or at least of reduced toxicity to recipients at the used dosages and concentrations, and is compatible with other ingredients of the formulation comprising the drug, agent or binding molecule.

As used herein, the term "therapeutically effective amount" refers to an amount of the binding molecule of the invention that is effective for prevention or treatment before or after exposure to the rabies virus.

The present inventors have ascertained that, when amino acid positions 33, 34, 35, 38, 200, 202 and 215 of the rabies virus G protein other than a signal peptide are substituted with other amino acid residues using a shotgun mutagenesis method, the binding activity to an antibody according to the present invention may remarkably decrease, from which the corresponding site is verified to be an epitope of the rabies virus G protein. Also, when amino acid positions 331 and 333 of the rabies virus G protein are substituted with other amino acid residues using a shotgun mutagenesis method, the binding activity to another antibody according to the present invention may remarkably decrease, from which the corresponding site is verified to be an epitope of the rabies virus G protein. Also, in an antibody cocktail comprising the above two antibodies that are mixed, neutralizing activity against the rabies virus can be confirmed without any interference by binding to different epitopes. Thereby, the epitope of the present invention, the antibody binding thereto, and the antibody cocktail thereof can be found to be efficiently useful to treat patients infected with the rabies virus derived from a wide range of individuals.

Advantageous Effects

According to the present invention, different epitope sites of the rabies virus G protein have been identified, and binding molecules that bind thereto and a cocktail thereof have also been confirmed to have neutralizing activity against various rabies viruses. Therefore, the rabies virus G protein epitope and the rabies-virus-neutralizing binding molecule that binds specifically thereto are useful in the diagnosis, prevention or treatment of rabies.

BRIEF DESCRIPTION OF DRAWING

FIG. 1 shows the survival rates of mice against SV2 virus in an animal test.

MODE FOR INVENTION

A better understanding of the present invention may be obtained via the following examples, which are set forth to illustrate, but are not to be construed as limiting the scope of the present invention. The documents cited herein are incorporated by reference into this application.

Example 1: Epitope Identification of Antibody

In order to identify epitopes of two antibodies (hereinafter, referred to as "antibody 1" or "antibody 2") among four antibodies finally selected in Example 4 disclosed in Korean Patent Application No. 10-2014-0178030, a single mutation in the rabies virus G protein (SEQ ID NO:1) was induced, and the binding activity of antibody 1 and antibody 2 to each mutant was evaluated. The preparation of each mutant and the analysis of the binding activity of antibody 1 and antibody 2 thereto were performed using a shotgun mutagenesis method (J Am Chem Soc. 2009; 131(20): 6952-6954) of Integral Molecular, USA.

A shotgun mutagenesis method enables the expression and analysis of a library of mutated target proteins in eukaryotic cells. Particularly, all residues of the target protein may be mutated with different amino acids and may be expressed in a mammalian cell line to analyze changes in monoclonal antibody (MAb) binding or function.

A shotgun mutagenesis method was performed in two steps, in which the G protein expression plasmid of the wild-type rabies virus CVS-11 strain was prepared and expressed in a mammalian cell line, after which the antibody concentration for binding activity analysis of antibody 1 and antibody 2 was optimized.

Thereafter, a mutant library (hereinafter, referred to as "single mutant library"), in which respective amino acid residues in the G protein of the rabies virus CVS-11 strain were substituted with other amino acids, was prepared using a shotgun mutagenesis method, and the binding activity thereof to the antibody was analyzed, and thus the epitopes of antibody 1 and antibody 2 were confirmed.

Example 1-1: Preparation of Plasmid Expressing Rabies Virus G Protein

A plasmid was prepared using a gene (Genbank Ref # AAC34683.1) expressing the G protein of the rabies virus CVS-11 strain, and the C-terminus thereof was tagged with V5/HIS6 in order to verify the expression thereof. Next, the plasmid was expressed in HEK293 cells. The corresponding plasmid was temporarily transfected to the HEK293 cells, followed by incubating the plasmid containing only a vector as a negative control group and a positive control group, that is, a structure (WT RABV) expressing the rabies virus G proteome, in a 384-well plate for one day.

Example 1-2: Preparation of Single Mutant Library of Rabies Virus G Protein

A single mutant library, in which each of amino acid residues at positions 1~505 of rabies virus G protein (SEQ ID NO:2), except for a signal peptide, was substituted with a different amino acid, was prepared using a shotgun mutagenesis method. The plasmid prepared in Example 1-1 was used as a parent plasmid. Alanine scanning mutagenesis was performed as a mutagenesis strategy to produce 505 mutant clones (hereinafter referred to as "alanine scanning mutants"). The alanine scanning mutagenesis is a method of substituting the protein amino acid with alanine to evaluate the contribution of the specific amino acid site to the function, stability or external response of the whole protein. Also, using an escape mutant virus testing method (Korean Patent Application No. 10-2014-0178030), each of the amino acids at positions 34, 210, 331, 336 and 413 of the rabies virus G protein was substituted not with alanine but with the other amino acid residue to produce single mutant clones (hereinafter referred to as "customized mutants"). Therefore, the total library size consisted of 512 mutant clones, as shown in Table 1 below.

TABLE 1

Properties of library used for epitope identification

| Clone name | Clone | No. of clones |
|---|---|---|
| Alanine scanning mutants | Substitution of each of rabies G protein amino acids 1-505 → Ala(A) Substitution of Ala(A) in rabies G protein amino acids 1-505 → Ser(S) | 505 |
| Customized mutants | Substitution of rabies G protein amino acid 34 Gly(G) → Val(V) Substitution of rabies G protein amino acid 34 Gly(G) → Glu(E) Substitution of rabies G protein amino acid 34 Gly(G) → Arg(R) Substitution of rabies G protein amino acid 210 Val(V) → Glu(E) Substitution of rabies G protein amino acid 331 Ser(S) → Leu(L) Substitution of rabies G protein amino acid 336 Asn(N) → Lys(K) Substitution of rabies G protein amino acid 413 Glu(E) → Asp(D) | 7 |
| | Total number | 512 |

*Amino acid position was numbered except for the signal peptide of rabies virus G protein

Example 1-3: Epitope Identification of Antibody

Example 1-3-1: Epitope Identification of Antibody Using Alanine Scanning Mutant In order to identify epitopes of antibody 1 and antibody 2, the binding activity to antibody 1 and antibody 2 was analyzed using the alanine scanning mutant library prepared in Example 1-2.

In order to evaluate the binding of the alanine scanning mutant library of Example 1-2 and antibody 1 and antibody 2, immunofluorescent FACS was performed two times, and thus mutants were selected.

When the whole antibody body of antibody 1 and antibody 2 was used as it is for the epitope analysis test, the corresponding analysis discrimination was decreased. Hence, antibody 1 and antibody 2 were treated with papain, whereby the Fc portion was removed from the antibody and only the Fab portion was left behind, thus determining the use of Fab of antibody 1 and Fab of antibody 2. Through the test using Fc-free Fab, a secondary antibody for analytical detection was a Fab-specific Alexa Fluor 488-conjugated secondary antibody (Jackson Immunoresearch Alexa fluor488 Goat anti-human F(ab')2 fragment).

Also, the epitope analysis test was performed under the condition that the optimal concentration of antibody 1 Fab was 0.33 μg/ml and the optimal concentration of antibody 2 Fab was 0.33 μg/ml. As the control antibodies, Abcam 1C5 (Abcam Inc.) and QED 20501 (QED Bioscience Inc.) antibodies were used, and analysis was performed under the condition that the optimal concentration of the control antibody Abcam 1C5 was 0.25 μg/ml and the optimal concentration of the control antibody QED 20501 was 0.5 μg/ml.

In the library selection, selected were alanine scanning mutants expressed over 80% of the control antibody Abcam 1C5 or QED 20501 and simultaneously less than 15% of antibody 1 Fab or antibody 2 Fab, compared to the binding reactivity to the positive control group of Example 1-1.

TABLE 2

| | Binding reactivity (% WT) | | | |
|---|---|---|---|---|
| Mutant | Antibody 1 Fab | Antibody 2 Fab | Abcam 105 Mab | QED 20501 MAb |
| E33A | 1.3 | 59.3 | 81.2 | 93.4 |
| G34A | −0.3 | 95.9 | 98.2 | 91.7 |
| C35A | 3.9 | 83.7 | 101.6 | 94.9 |
| L38A | 5.4 | 130.2 | 127.6 | 113.8 |
| A200S | 10.5 | 102.9 | 109.1 | 87.6 |
| K202A | 4.2 | 132 | 113 | 105.5 |
| L215A | 6.6 | 100.1 | 101.7 | 100.0 |
| R333A | 68.6 | 5.4 | 103.1 | 109.1 |

As is apparent from the results of Table 2, in the case of antibody 1, a total of seven alanine scanning mutants were selected, and the epitope sites of antibody 1 were identified as being located at amino acid positions 33, 34, 35, 38, 200, 202 and 215 of the rabies virus G protein through the selected mutants.

In the case of antibody 2, a total of one alanine scanning mutant was selected, and the epitope site of antibody 2 was identified as being located at amino acid position 333 of the rabies virus G protein through the selected mutant.

Example 1-3-2: Epitope Identification of Antibody Using Customized Mutant

In order to identify epitopes of antibody 1 and antibody 2, the binding activity to antibody 1 and antibody 2 was analyzed using the customized mutant library prepared in Example 1-2.

In order to evaluate the binding of the customized mutant library of Example 1-2 and antibody 1 and antibody 2, immunofluorescent FACS was performed as in Example 1-3-1, and mutants were selected. The selection results are shown in Table 3 below. Here, Anti-V5 was used as an analytical control group for confirming the expression of the rabies virus G protein with the expression vector.

TABLE 3

| Mutant | Binding reactivity (% WT) | | | | |
|---|---|---|---|---|---|
|  | Antibody 1 Fab | Antibody 2 Fab | Abeam 105 MAb | QED 20501 MAb | Anti-V5 |
| G34V | 2.1 | 108 | 101 | 74.6 | 91.9 |
| G34E | 1.4 | 138 | 167 | 124 | 75.2 |
| G34R | 1.4 | 76.6 | 120 | 56.7 | 72.3 |
| V210E | 23.9 | 8.3 | 1.6 | −1 | 85.9 |
| S331L | 60.5 | −0.1 | 82.3 | 50.4 | 111 |
| N336K | 85.3 | 101 | 84.4 | 59 | 96.1 |
| E413D | 78.6 | 77.7 | 115 | 40.7 | 80.4 |

As is apparent from the results of able 3, in the case of antibody 1, three customized mutants were selected, and the epitope site of antibody 1 was identified as being located at amino acid position 34 of the rabies virus G protein through the selected mutants.

In the case of antibody 2, one customized mutant was selected, and the epitope site of antibody 2 was identified as being located at amino acid position 331 of the rabies virus G protein through the selected mutant.

Example 1-3-3: Results of Epitope Identification of Antibody

Based on the results of Examples 1-3-1 and 1-3-2, the epitope of antibody 1 was found to be located at amino acid positions 33, 34, 35, 38, 200, 202 and 215 of the rabies virus G protein (SEQ ID NO:2), and the epitope of antibody 2 was found to be located at amino acid positions 331 and 333 of the rabies virus G protein, as shown in Table 4 below.

The rabies virus binding sites are represented as the antigenic sites of surface glycoprotein of the rabies virus, and the antigenic structure of rabies glycoprotein for each site was first defined by Lafon et al. (J. Gen. Virol. 64:843-8451 1983). The currently identified rabies virus binding sites were classified into antigenic sites I, II, III, IV, and a, and were defined by Marissen et al. (J Virol. 2005 April; 79(8):4672-8.).

TABLE 4

| Antibody ID | No. | Amino acid residue | | Rabies virus binding site |
|---|---|---|---|---|
|  |  | Amino acid mutant | Amino acid position* |  |
| Antibody 1 | 1 | Glu(E)-->Ala(A) | 33 | Not known |
|  | 2 | Gly(G)-->Ala(A) | 34 | Antigenic site II |
|  | 3 | Cys(C)-->Ala(A) | 35 | Antigenic site II |
|  | 4 | Leu(L)-->Ala(A) | 38 | Antigenic site II |
|  | 5 | Ala(A)-->Ser(S) | 200 | Antigenic site II |

TABLE 4-continued

| Antibody ID | No. | Amino acid residue | | Rabies virus binding site |
|---|---|---|---|---|
|  |  | Amino acid mutant | Amino acid position* |  |
|  | 6 | Lys(K)-->Ala(A) | 202 | Not known |
|  | 7 | Leu(L)-->Ala(A) | 215 | Not known |
| Antibody 2 | 1 | Ser(S)-->Leu(L) | 331 | Antigenic site III |
|  | 2 | Arg(R)-->Ala(A) | 333 | Antigenic site III |

*Amino acid position was numbered except for the signal peptide of the rabies virus G protein

Example 2: Determination of Antigen-Antibody Binding Affinity Using Surface Plasmon Resonance Technique A surface plasmon resonance assay (Biacore Inc.) was used to determine the binding affinity of the antibody by epidemiological measurement of the forward and reverse reaction rate constants. Therefore, the antigen-antibody binding affinity of antibody 1 and antibody 2 was determined using a surface plasmon resonance technique.

Particularly, the binding affinity of purified rabies virus G protein and antibody 1 and antibody 2 was determined through a surface plasmon resonance assay by means of a Biacore T200 (GE Healthcare) using an analytical buffer HBS-EP (10 mM HEPES [pH 7.4], 150 mM NaCl, 3 mM EDTA and 0.005% surfactant P20) at 25° C. 50 µg/ml rabies virus G protein diluted in 10 mM sodium acetate (pH 5.0) was directly immobilized by about 500 RU on a CM5 biosensor chip using an amine coupling kit in accordance with the manufacturer's guidelines and procedures. The unreacted portion of the biosensor surface was blocked with ethanolamine. For the reaction analysis, Biacore T200 control software and Biacore T200 evaluation software were used. Antibody 1 and antibody 2 were diluted in a HBS-EP buffer. During the assay, all measurements were performed using, as a control group, the biosensor surface having no immobilized rabies virus G protein. The association and dissociation rate constants Ka ($M^{-1}s^{-1}$) and Kd ($s^{-1}$) were determined at a flow rate of 30 µl/min. The rate constant was obtained by measuring the binding in the antibody concentration range of 2.46 to 200 nM through a three-fold serial dilution and using the buffer as a control group. Subsequently, the equilibrium dissociation constant KD (M) for the reaction between the antibody and the target antigen was calculated using the following equation from the reaction rate constants: KD=Kd/Ka. The binding was recorded by calculating the function of time and reaction rate constant.

Based on the results thereof, as shown in Table 5 below, the binding affinity of antibody 1 and antibody 2 to the purified rabies virus G protein was determined. Both antibody 1 and antibody 2 exhibited high affinity to the rabies virus G protein.

TABLE 5

| Measurement of binding affinity using rabies virus G protein | | | | |
|---|---|---|---|---|
| Sample | ka1 (1/Ms) | kd1 (1/s) | KD | AVR KD |
| Antibody 1 | 2.52E+05 | 9.39E−04 | 3.73E−09 | 4.54E−09 |
|  | 2.14E+05 | 1.15E−03 | 5.36E−09 |  |
| Antibody 2 | 2.11E+06 | 0.0005743 | 2.72E−10 | 2.24E−10 |
|  | 1.54E+06 | 2.70E−04 | 1.75E−10 |  |

Example 3: Evaluation of Neutralizing Activity of Antibody Against Escape Virus Produced by CR4098 Antibody

Example 3-1: Production of Escape Virus for CR4098 Antibody

The DNA sequence for the CR4098 antibody (Crucell) was verified with reference to U.S. Pat. No. 7,579,446 and the NCBI (National Center for Biotechnology Information) database, and was synthesized in Enzynomics Co. Ltd. (located in Yuseong-gu, Daejeon), cloned to a pCT146 expression vector (according to Korean Patent Application No. 10-2014-0178030), and then delivered to Celltrion Inc. The sequence of the synthesized portion was confirmed through restriction enzyme cleavage analysis and DNA sequencing. The CR4098 antibody was produced in the F2N78 cell line through a transient transduction method.

For intracellular transient transduction a formulation for transfecting plasmid DNA into eukaryotic cells, FREESTYLE™ Max (Invitrogen, 16447-100), was used, and transduction was performed in accordance with the manufacturer's manual. The day before transduction, F2N78 cells (Korean Patent No. 10-1005967, Patentee: Celltrion) growing on an EX-CELL 293 serum-free medium (Sigma, 14571C: hereinafter referred to as "EX-CELL 293 medium") were centrifuged, the medium was replaced with a FreeStyle293 serum-free medium (Gibco, 12338), and the cells were inoculated in an amount of 50 ml each (a total of 100 ml) at a cell concentration of $0.8\times10^6$ per ml using two 250 ml shaker flasks. On the day of transduction, each of 125 μg of pCT178 DNA containing an antibody gene and 125 μl of the FREESTYLE™ Max reagent formulation for transfecting plasmid DNA into eukaryotic cells was diluted to a volume of 2 ml using an OptiPRO SFM II medium (Invitrogen, 12309), and gently mixed. The immediately diluted FreeStyle™ Max reagent formulation solution was mixed with a DNA-diluted solution and then reacted at room temperature for 17 min. During the reaction at room temperature for 17 min, the number of inoculated F2N cells to be used for transduction was counted, and the cell concentration was diluted to $1.0\times10^6$ using the FreeStyle293 medium. After 17 min, transduction was carried out by treating a mixed solution of DNA and the formulation for transfecting plasmid DNA into eukaryotic cells, FREESTYLE™ Max reagent, with F2N cells. The day after transduction, the same amount of EX-CELL 293 medium was added to the transduced cells and incubated for 7 days, thereby producing the CR4098 antibody.

Thereafter, CR4098 was used to perform the test for producing the escape mutant virus for the corresponding antibody.

A rabies virus CVS-1 strain having an infectivity of $10^6$ per ml was subjected to a 1.5-fold serial dilution in a 96-well cell culture plate and then reacted with 10~40 IU/ml CR4098 antibody at 37° C. for 1 hr. After reaction for 1 hr, $2\times10^5$ cells/ml BHK cells were added and incubated for 3 days. After 3 days, the virus was obtained, the cells were immobilized, and the expression of rabies nucleocapsid protein was measured through staining in order to evaluate whether the cells were infected with the CVS-11 strain (JENO Biotech, 9061). In the second passage, an increased amount of CR4098 antibody was added to the virus obtained in the first passage, and the same test as above was repeated. In the first or second passage, virus 4~5 clones, in which the virus, obtained from the wells that had not been infected or had been little infected with the rabies virus CVS-11 strain, was confirmed to cause infection or to increase the extent of infection despite the addition of the CR4098 antibody in a gradually increasing amount, were amplified, after which RNA was isolated using a QIAamp Viral RNA Mini kit (QIAGEN, 52904).

Using RNA as a template, cDNA was synthesized by means of a SuperScriptIII First-strand Synthesis system for RT-PCR (Invitrogen, 18080-051), and then amplified by Takara ExTaq (Takara, RR001A), followed by sequencing. Based on the results of sequencing, the changed sequence of the escape mutant virus for the CR4098 antibody was showed in N336K.

Example 3-2: Evaluation of Neutralizing Activity of Antibody Against Escape Virus Produced by CR4098 Antibody Whether antibody 1 and antibody 2 had neutralizing activity against the escape virus (N336K) produced by the CR4098 antibody in Example 3-1 was evaluated.

The test for the neutralizing activity was performed using a FAVNT method. The Fluorescent Antibody Virus-Neutralizing Test (FAVNT) is a test method for determining the level of rabies virus antibody in human or animal serum through a cell culture method.

In the test method of FAVNT, the dilution testing antibody (or HRIG) and a predetermined amount of rabies virus [100 TCID50/0.1 ml] were placed in a 96-well plate and reacted for 60 min, and baby hamster kidney cells were incubated for 36~48 hr together with a culture medium containing 10% bovine serum (Eagle's minimum essential medium). After the incubation, the cells were immobilized, and then the anti-rabies antibody, ABC kit (VECTASTAIN) and DAB kit (VECTASTAIN) were used to stain the cells infected with the rabies virus. Finally, the number of stained cells was counted and the neutralizing activity of the test antibody relative to HRIG, the neutralizing activity of which is precisely known, was calculated.

As results thereof, as shown in Table 6 below, both antibody 1 and antibody 2 exhibited neutralizing activity against the CR4098 antibody escape virus (N336K), and only the CR4098 antibody had no neutralizing activity.

TABLE 6

Results of evaluation of neutralizing activity of antibody against escape virus produced by CR4098 antibody

| Virus | Antibody | IU/mg |
|---|---|---|
| CR4098 antibody escape virus (N336K) | CR4098 | All infected |
| | Antibody 1 | 1352 |
| | Antibody 2 | 3081 |

Example 4: Evaluation of Neutralizing Activity of Antibody Against Various Kinds of Rabies Virus Approximately 50 varieties of rabies virus from around the world were tested for in-vitro neutralizing activity of antibody 1 and antibody 2 through RFFIT. The results are shown in Table 7 below.

Upon the neutralizing activity testing, a Rapid Fluorescent Focus Inhibition Test (RFFIT) was performed to measure the activity of the antibody exposed by the rabies virus antigen. The neutralizing antibody was induced by glycoprotein on the outer surface of the virus. The Disease Control Center adopted the RFFIT method, which is rapid, economic, sensitive and reproducible.

Like FAVNT, RFFIT is a test method for determining the level of rabies virus antibody in human or animal serum through the cell culture method. The immunofluorescent staining was used to evaluate virus amplification and required about 20 hr.

RFFIT was performed in a multi-well slide using the mixed dilution test serum and the predetermined amount of rabies virus [50-50% Fluorescing Foci Doses (50 FFD50)/0.1 ml]. The mixed slide containing neuroblastoma and culture medium (Eagle's minimum essential medium) and 10% bovine serum was incubated in a 37° C. carbon dioxide incubator for 90 min. The form of serum-virus-cell was incubated for 20 hr in a 37° C. carbon dioxide incubator. Thereafter, incubation, washing, immobilization, and staining of the rabies virus conjugate with a label were performed, and observation was conducted using a fluorescence microscope.

TABLE 7

Results of evaluation of neutralizing activity of antibody against various kinds of rabies virus

| | | | Antibody 1 | Antibody 2 |
|---|---|---|---|---|
| | | | Working conc.(μg/ml) | |
| No. | Virus | ID | 0.20 | |
| 1 | Mongoose RSAMongoose, South Africa | Titer | 270 | 320 |
| | | IU/mL | 7.7 | 9.1 |
| | | IU/mg | 7714 | 9143 |
| 2 | Dog TunDog, Tunisia | Titer | 230 | 270 |
| | | IU/mL | 2.3 | 2.7 |
| | | IU/mg | 2300 | 2700 |
| 3 | Dog thaiDog, Thailand | Titer | 320 | 1300 |
| | | IU/mL | 2.3 | 9.3 |
| | | IU/mg | 2286 | 9286 |
| 4 | Dog sonDog, Mexico | Titer | 340 | 1100 |
| | | IU/mL | 2.7 | 8.8 |
| | | IU/mg | 2720 | 8800 |
| 5 | Phi 002 (231)Human/dog, Philippines | Titer | 250 | 250 |
| | | IU/mL | 2.5 | 2.5 |
| | | IU/mg | 2500 | 2500 |
| 6 | DR MXBat, Mexico | Titer | 250 | 180 |
| | | IU/mL | 2.4 | 1.7 |
| | | IU/lng | 2381 | 1714 |
| 7 | DR BrazilBat, Brazil | Titer | 56 | 45 |
| | | IU/mL | 2.2 | 1.8 |
| | | IU/mg | 2240 | 1800 |
| 8 | WA BatBat, Washington, USA | Titer | 270 | 250 |
| | | IU/mL | 2.2 | 2.0 |
| | | IU/mg | 2160 | 2000 |
| 9 | rv61Human (ex, dog),UK(ex, India) | Titer | 200 | 280 |
| | | IU/mL | 1.7 | 2.4 |
| | | IU/mg | 1739 | 2435 |
| 10 | AL BatBat, California, USA | Titer | 1100 | 1100 |
| | | IU/mL | 7.6 | 7.6 |
| | | IU/mg | 7586 | 7586 |
| 11 | AZ BatBat , Arizona | Titer | 125 | 1300 |
| | | IU/mL | 1.1 | 11.3 |
| | | IU/mg | 1087 | 11304 |
| 12 | phi dogHuman/dog, Philippines | Titer | 75 | 280 |
| | | IU/mL | 0.28 | 1.04 |
| | | IU/mg | 1389 | 5185 |
| 13 | Rv342 ChinaCow/dog, China | Titer | 280 | 1300 |
| | | IU/mL | 0.5 | 2.4 |
| | | IU/mg | 2545 | 11818 |
| 14 | TX SK 4384Skunk, Texas, USA | Titer | 75 | 250 |
| | | IU/mL | 0.21 | 0.71 |
| | | IU/mg | 1071 | 3571 |
| 15 | AK FXArctic Fox, Alaska, USA Failed | Titer | 60 | 270 |
| | | IU/mL | 0.44 | 2.00 |
| | | IU/mg | 2222 | 10000 |
| 16 | Gray FX-AZ (AZ fox)Gray Fox, Arizona, USA | Titer | 16 | 170 |
| | | IU/mL | 0.53 | 5.67 |
| | | IU/mg | 2667 | 28333 |
| 17 | 323RDog/Coyote, Texas, USA | Titer | 60 | 625 |
| | | IU/mL | 0.33 | 3.47 |
| | | IU/mg | 1667 | 17361 |
| 18 | RVHNHuman (ex, wolf), Russia, Arctic | Titer | 54 | 42 |
| | | IU/mL | 0.40 | 0.31 |
| | | IU/mg | 2000 | 1556 |
| 19 | TN-269Bat, Tennessee, USA | Titer | 145 | 390 |
| | | IU/mL | 1.16 | 3.12 |
| | | IU/mg | 5800 | 15600 |
| 20 | China dog 2005Dog, China | Titer | 12 | 13 |
| | | IU/mL | 0.43 | 0.46 |
| | | IU/mg | 2143 | 2321 |
| 21 | TN410Bat, Tennessee, USA | Titer | 19 | 200 |
| | | IU/mL | 0.51 | 5.33 |
| | | IU/mg | 2533 | 26667 |
| 22 | Dog ArgDog, Argentina | Titer | 145 | 170 |
| | | IU/mL | 0.36 | 0.43 |
| | | IU/mg | 1813 | 2125 |
| 23 | TX SK 4380Skunk, Texas, USA | Titer | 50 | 70 |
| | | IU/mL | 0.40 | 0.56 |
| | | IU/mg | 2000 | 2800 |
| 24 | RACRaccoon, Georgia, USA | Titer | 95 | 145 |
| | | IU/mL | 0.70 | 1.07 |
| | | IU/mg | 3519 | 5370 |
| 25 | TX CoyoteCoyote, Texas, USA | Titer | 56 | 170 |
| | | IU/mL | 0.33 | 1.00 |
| | | IU/mg | 1647 | 5000 |
| 26 | Mongoose PRMongoose, Puerto-Rico | Titer | 54 | 56 |
| | | IU/mL | 0.39 | 0.40 |
| | | IU/mg | 1929 | 2000 |
| 27 | I-151Dog, India | Titer | 125 | 320 |
| | | IU/mL | 0.74 | 1.88 |
| | | IU/mg | 3676 | 9412 |
| 28 | Sri LankaCow, Sri Lanka | Titer | 54 | 50 |
| | | IU/mL | 0.43 | 0.40 |
| | | IU/mg | 2160 | 2000 |
| 29 | Wu ABLVAustralian bat lyssa, Genotype 7 | Titer | 250 | 440 |
| | | IU/mL | 0.38 | 0.68 |
| | | IU/mg | 1923 | 3385 |
| 30 | ABV (SM 4476) Australian bat lyssa, Genotype 7 | Titer | 54 | 210 |
| | | IU/mL | 0.40 | 1.56 |
| | | IU/mg | 2000 | 7778 |
| 31 | 3860 CA BatBat, California, USA | Titer | 56 | 210 |
| | | IU/mL | 0.40 | 1.50 |
| | | IU/mg | 2000 | 7500 |
| 32 | Gabon dogDog, Gabon | Titer | 65 | 170 |
| | | IU/mL | 0.41 | 1.06 |
| | | IU/mg | 2031 | 5313 |
| 33 | CVS-11 | Titer | 70 | 250 |
| | | IU/mL | 0.41 | 1.47 |
| | | IU/mg | 2059 | 7353 |
| 34 | EBLV 1 A09-3484Genotype 5 | Titer | 56 | 540 |
| | | IU/mL | 0.56 | 5.40 |
| | | IU/mg | 2800 | 27000 |
| 35 | EBLV 2 A03-4659Genotype 6 | Titer | 54 | 280 |
| | | IU/mL | 0.60 | 3.11 |
| | | IU/mg | 3000 | 15556 |
| 36 | DuvenhageGenotype 4 | Titer | 13 | 180 |
| | | IU/mL | 0.44 | 7.20 |
| | | IU/mg | 2200 | 36000 |
| 37 | EBLV 1 A09-3485Genotype 5 | Titer | 50 | 180 |
| | | IU/mL | 1.85 | 6.67 |
| | | IU/mg | 9259 | 33333 |
| 38 | EBLV 2 A09-3483Genotype 6 | Titer | 50 | 125 |
| | | IU/mL | 2.22 | 5.56 |
| | | IU/mg | 11111 | 27778 |
| 39 | CASKSkunk, California, USA | Titer | 50 | 54 |
| | | IU/mL | 0.40 | 0.43 |
| | | IU/mg | 2000 | 2160 |

TABLE 7-continued

Results of evaluation of neutralizing activity of antibody against various kinds of rabies virus

| No. | Virus | ID | Antibody 1 | Antibody 2 |
|---|---|---|---|---|
| | | | Working conc.(μg/ml) | |
| | | | 0.20 | |
| 40 | Bat EfBat, Pennsylvania, USA | Titer | 50 | 50 |
| | | IU/mL | 1.05 | 1.05 |
| | | IU/mg | 5263 | 5263 |
| 41 | C1434Bat, Alabama, USA | Titer | 19 | 36 |
| | | IU/mL | 0.51 | 0.96 |
| | | IU/mg | 2533 | 4800 |
| 42 | VA 399Bat, Virginia, USA | Titer | 10 | 50 |
| | | IU/mL | 0.56 | 2.78 |
| | | IU/mg | 2778 | 13889 |
| 43 | TN 132Bat, Tennessee, USA | Titer | 56 | 280 |
| | | IU/mL | 2.00 | 10.00 |
| | | IU/mg | 10000 | 50000 |
| 44 | TXFXGray fox, TX | Titer | 56 | 250 |
| | | IU/mL | 0.41 | 1.85 |
| | | IU/mg | 2074 | 9259 |
| 45 | I-148Dog, India | Titer | 13 | 10 |
| | | IU/mL | 0.52 | 0.40 |
| | | IU/mg | 2600 | 2000 |
| 46 | LC NYBat, New York, USA | Titer | 11 | 45 |
| | | IU/mL | 0.52 | 2.14 |
| | | IU/mg | 2619 | 10714 |
| 47 | 857rRaccoon dog, Russia, Far East | Titer | 56 | 54 |
| | | IU/mL | 2.80 | 2.70 |
| | | IU/mg | 2800 | 2700 |
| 48 | NC SKSkunk, Wisconsin, USA | Titer | 280 | 270 |
| | | IU/mL | 2.24 | 2.16 |
| | | IU/mg | 2240 | 2160 |
| 49 | MI1625Bat, Tennessee, USA | Titer | 11 | 70 |
| | | IU/mL | 0.39 | 2.50 |
| | | IU/mg | 1964 | 12500 |
| 50 | MyotisBat, Washington, USA | Titer | 230 | 280 |
| | | IU/mL | 1.64 | 2.00 |
| | | IU/mg | 8214 | 10000 |
| 51 | ERA | Titer | 50 | 250 |
| | | IU/mL | 0.36 | 1.79 |
| | | IU/mg | 1786 | 8929 |

Example 5: Evaluation of Neutralizing Activity of Antibody Against Rabies Virus Isolated in India Example 5-1: In-Vitro Test Using antibody 1, antibody 2 and an antibody cocktail (antibody 1+antibody 2), a wild-type virus of Table 8 below, flourishing in India, was subjected to RFFIT as in Example 4. The test was conducted in the National Institute of Mental Health and Neuro-Sciences (NIMHANS), India. Each antibody was at a concentration of about 1 μg, and testing was carried out in Neuro-2a cells with 100 $FFD_{50}$ of each virus of Table 8 below. The results of RFFIT exhibited neutralizing activity against each virus in all of three antibodies.

TABLE 8

Rabies virus isolated in India

| Virus abbreviation | Virus-isolated animal | Virus-isolated area |
|---|---|---|
| SV1 | Dog | Kerala, India |
| SV2 | Dog | Kerala, India |
| SV3 | Human | Karnataka, India |
| SV4 | Human | Karnataka, India |
| SV5 | Dog | Chennai, Tamilnadu, India |
| SV6 | Dog | Chennai, Tamilnadu, India |

Example 5-2: In-Vivo Test

In-vivo testing was performed in mice following the in-vitro testing of Example 5-1. As shown in Table 9 below, all antibodies in animal test groups exhibited high neutralizing activity. 10 mice were used in each animal test group, and the virus used was 100 LD50 (in 0.1 mL). 3 hr after virus inoculation (muscle injection), each antibody (about 1 μg) was inoculated at the same position (muscle injection), after which the survival rate was observed for 30 days. FIG. 1 is a graph showing the mouse survival rate against SV2 virus among a total of six viruses (SV1~SV6) in an animal test.

In the present animal test, the survival rate against each of SV1 to SV6 viruses is shown in Table 9 below.

TABLE 9

Results of evaluation of neutralizing activity of antibody against rabies virus isolated in India through animal testing

| | SV1 | SV2 | SV3 | SV4 | SV5 | SV6 |
|---|---|---|---|---|---|---|
| Antibody 1 | 100 | 100 | 100 | 100 | 100 | 100 |
| Antibody 2 | 80 | 90 | 90 | 80 | 90 | 90 |
| Antibody 1 + Antibody 2 | 100 | 100 | 100 | 100 | 100 | 100 |
| Control group | 0 | 0 | 0 | 0 | 0 | 0 |

Example 6: Evaluation of Interference Effect of Cocktail of Antibody 1 and Antibody 2

Example 6-1: Evaluation of Interference Effect of Cocktail of Antibody 1 and Antibody 2 Using Test for Measuring Neutralizing Activity Against Wild-Type Rabies Virus and Rabies Virus CVS-11 Strain Using antibody 1, antibody 2 and an antibody cocktail (antibody 1+antibody 2), twelve wild-type rabies viruses and the rabies virus CVS-11 strain were subjected to RFFIT as in Example 4.

As set forth in Table 10 below, all of antibody 1, antibody 2 and the cocktail comprising antibody 1 and antibody 2 mixed at the same ratio exhibited superior neutralizing activity against twelve wild-type rabies viruses and the rabies virus CVS-11 strain, whereby antibody 1 and antibody 2 in the cocktail were confirmed to have no interference effect upon biological neutralizing activity evaluation.

TABLE 10

Results of evaluation of neutralizing activity of antibody cocktail against various kinds of rabies virus

| No. | Virus | Antibody 1 (IU/mg) | Antibody 2 (IU/mg) | Cocktail (1:1) (IU/mg) |
|---|---|---|---|---|
| 1 | LC NY Bat, New York, USA | 2619 | 10714 | 8571 |
| 2 | Bat Ef Bat, Pennsylvania, USA | 5263 | 5263 | 4421 |
| 3 | TX Coyote Coyote, Texas, USA | 1647 | 5000 | 2500 |
| 4 | 1-151 Dog, India | 3676 | 9412 | 5000 |
| 5 | Gabon dog Dog, Gabon | 2031 | 5313 | 4531 |
| 6 | Sri Lanka Cow, Sri Lanka | 2160 | 2000 | 2000 |
| 7 | NC SK Skunk, Wisconsin, USA | 2240 | 2160 | 2240 |
| 8 | China dog 2005 Dog, China | 2143 | 2321 | 1964 |
| 9 | Dog thai Dog, Thailand | 2286 | 9286 | 7857 |
| 10 | phi dog Human/dog, Philippines | 1389 | 5185 | 4630 |
| 11 | Mongoose RSA Mongoose, South Africa | 7714 | 9143 | 9143 |
| 12 | Myotis Bat, Washington, USA | 8214 | 10000 | 8929 |
| 13 | CVS-11 | 2059 | 7353 | 6765 |

Example 6-2: Evaluation of Interference Effect of Cocktail of Antibody 1 and Antibody 2 Using Molar Excess Testing Whether antibody 1 and antibody 2 exhibited the interference effect was also evaluated through molar excess testing. To this end, the concentration ratio of two antibodies was set in the range of 1/9 to 9/1 for the rabies virus CVS-11 strain tested in Example 6-1, and REFIT was performed three times as in Example 4. The results are shown in Tables 11 and 12 below.

Through the testing at different concentration ratios of antibody 1 and antibody 2, even when the ratio of antibody 1 and antibody 2 was adjusted to 1:9 to 9:1, all of antibody 1, antibody 2, and the cocktail of antibody 1 and antibody 2 exhibited the rabies-virus-neutralizing activity shown in Tables 11 and 12 below.

TABLE 11

Evaluation of neutralizing activity of antibody cocktail against rabies virus CVS-11 strain
Test Results (IU/mg) (Measurement using antibody 1)

| | Antibody 1 (%) | Antibody 2 (%) | 1 | 2 | 3 | Mean | Standard deviation |
|---|---|---|---|---|---|---|---|
| A | 0 | 100 | N/A | N/A | N/A | N/A | N/A |
| B | 10 | 90 | 45000 | 34185 | 102556 | 60581 | 36752 |
| C | 25 | 75 | 41023 | 18000 | 23688 | 27570 | 11992 |
| D | 50 | 50 | 6837 | 3948 | 11844 | 7543 | 3995 |
| E | 75 | 25 | 2000 | 1519 | 3464 | 2328 | 1013 |
| F | 90 | 10 | 962 | 731 | 1667 | 1120 | 487 |
| G | 100 | 0 | 380 | 380 | 658 | 473 | 161 |

TABLE 12

Evaluation of neutralizing activity of antibody cocktail against rabies virus CVS-11 strain
Test Results (IU/mg) (Measurement using antibody 2)

| | Antibody 1 (%) | Antibody 2 (%) | 1 | 2 | 3 | Mean | Standard deviation |
|---|---|---|---|---|---|---|---|
| A | 0 | 100 | 7793 | 4500 | 10256 | 7516 | 2888 |
| B | 10 | 90 | 5000 | 3798 | 11395 | 6731 | 4084 |
| C | 25 | 75 | 13674 | 6000 | 7896 | 9190 | 3997 |
| D | 50 | 50 | 6837 | 3948 | 11844 | 7543 | 3995 |
| E | 75 | 25 | 6000 | 4558 | 10391 | 6983 | 3038 |
| F | 90 | 10 | 8659 | 6580 | 15000 | 10080 | 4386 |
| G | 100 | 0 | N/A | N/A | N/A | N/A | N/A |

Dunnett's test, one of the multiple comparison test methods, was used as a statistical analysis method to evaluate the significance of the neutralizing activity difference between the test group and the control group to confirm the interference effect. Particularly, if the adjusted p-value in the Dunnett analysis is greater than 0.05, which is a significance threshold, it is not significant, indicating no difference between groups being compared. On the other hand, if the adjusted p-value is less than 0.05, it indicates that there is a significant difference between the groups being compared. The results of Dunnett's analysis based on Tables 11 and 12 are respectively shown in Tables 13 and 14 below.

As set forth in Tables 13 and 14 below, in Table 13, the adjusted p-value was 0.05 or less only when the proportion of antibody 2 was 90% or more, indicating that there was no interference effect except for the case of 90% content of antibody 2. However, in the case where the proportion of antibody 2 is 90% or more, the interference effect may exist statistically, but it is considered to be due to the very strong neutralizing activity of antibody 2 and cannot be regarded as the interference effect. In Table 14, even when the proportion of antibody 1 was increased, the adjusted p-value was 0.05 or more, confirming that there was no interference effect. Therefore, it can be concluded that there is no interference effect between two antibodies at all concentrations.

TABLE 13

Multiple comparison test results for rabies virus CVS-11 strain at antibody 1 concentration
Least-squares mean difference

| Multiple comparison test | Estimate | Standard error | Degrees of freedom | t value | Probability > \|t\| | Adjusted p-value | Result |
|---|---|---|---|---|---|---|---|
| B vs G | 60108 | 12961 | 12 | 4.64 | 0.0006 | 0.0024 | Significant |
| C vs G | 27098 | 12961 | 12 | 2.09 | 0.0585 | 0.1958 | Not significant |
| D vs G | 7070.4 | 12961 | 12 | 0.55 | 0.5954 | 0.9718 | Not significant |
| E vs G | 1855.1 | 12961 | 12 | 0.14 | 0.8886 | 0.9999 | Not significant |
| F vs G | 647.41 | 12961 | 12 | 0.05 | 0.961 | 1 | Not significant |

TABLE 14

Multiple comparison test results for rabies virus CVS-11 strain at antibody 2 concentration
Least-squares mean difference

| Multiple comparison test | Estimate | Standard error | Degrees of freedom | t value | Probability > \|t\| | Adjusted p-value | Result |
|---|---|---|---|---|---|---|---|
| B vs A | −785.08 | 3080.8 | 12 | −0.25 | 0.8032 | 0.9991 | Not significant |
| C vs A | 1673.77 | 3080.8 | 12 | 0.54 | 0.5969 | 0.9723 | Not significant |
| D vs A | 26.7002 | 3080.8 | 12 | 0.01 | 0.9932 | 1 | Not significant |
| E vs A | −533.29 | 3080.8 | 12 | −0.17 | 0.8655 | 0.9999 | Not significant |
| F vs A | 2563.39 | 3080.8 | 12 | 0.83 | 0.4216 | 0.8691 | Not significant |

Although the preferred embodiments of the present invention have been disclosed for illustrative purposes, those skilled in the art will appreciate that a variety of modifications and equivalents able to substitute therefor may be provided, without departing from the scope and spirit of the invention as disclosed in the accompanying claims. Accordingly, the present invention is not intended to be limited to particular embodiments, which are merely disclosed as the best form for performing the present invention, and should be construed to include all embodiments falling within the accompanying claims.

The invention claimed is:

1. A rabies-virus-neutralizing antibody which binds to an epitope located between amino acid residues 33 and 215 or an epitope located between amino acid residues 331 and 333 of the wild-type rabies virus G protein, the sequence of which protein is set forth in SEQ ID NO:2, wherein the antibody comprises:

a) a heavy chain variable domain comprising the CDR1 of SEQ ID NO:3, the CDR2 of SEQ ID NO:4, and the CDR3 of SEQ ID NO:5; and b) a light chain variable domain comprising the CDR1 of SEQ ID NO:6, the CDR2 of SEQ ID NO:7, and the CDR3 of SEQ ID NO:8; or a) a heavy chain variable domain comprising the CDR1 of SEQ ID NO:9, the CDR2 of SEQ ID NO:10, and the CDR3 of SEQ ID NO:11; and b) a light chain variable domain comprising the CDR1 of SEQ ID NO:12, the CDR2 of SEQ ID NO:13, and the CDR3 of SEQ ID NO:14;

or a rabies-virus-neutralizing fragment of such an antibody.

2. The antibody of claim 1, wherein the binding molecule has a binding affinity ($K_D$) less than $1 \times 10^{-8}$ M.

3. The antibody of claim 1, wherein if the antibody comprises a) a heavy chain variable domain comprising the CDR1 of SEQ ID NO:3, the CDR2 of SEQ ID NO:4, and the CDR3 of SEQ ID NO:5; and b) a light chain variable domain comprising the CDR1 of SEQ ID NO:6, the CDR2 of SEQ ID NO:7, and the CDR3 of SEQ ID NO:8, the heavy chain variable region comprises the sequence set forth in SEQ ID NO:15.

4. The antibody of claim 1, wherein if the antibody comprises a) a heavy chain variable domain comprising the CDR1 of SEQ ID NO:3, the CDR2 of SEQ ID NO:4, and the CDR3 of SEQ ID NO:5; and b) a light chain variable domain comprising the CDR1 of SEQ ID NO:6, the CDR2 of SEQ ID NO:7, and the CDR3 of SEQ ID NO:8, the light chain variable region comprises the sequence set forth in SEQ ID NO:16.

5. The antibody of claim 1, wherein if the antibody comprises a) a heavy chain variable domain comprising the CDR1 of SEQ ID NO:9, the CDR2 of SEQ ID NO:10, and the CDR3 of SEQ ID NO:11; and b) a light chain variable domain comprising the CDR1 of SEQ ID NO:12, the CDR2 of SEQ ID NO:13, and the CDR3 of SEQ ID NO:14, the heavy chain variable region comprises the sequence set forth in SEQ ID NO:17.

6. The antibody of claim 1, wherein if the antibody comprises a) a heavy chain variable domain comprising the CDR1 of SEQ ID NO:9, the CDR2 of SEQ ID NO:10, and the CDR3 of SEQ ID NO:11; and b) a light chain variable domain comprising the CDR1 of SEQ ID NO:12, the CDR2 of SEQ ID NO:13, and the CDR3 of SEQ ID NO:14, the light chain variable region comprises the sequence set forth in SEQ ID NO:18.

7. The antibody of claim 3, wherein the sequence of the heavy chain is set forth in SEQ ID NO:19.

8. The antibody of claim 4, wherein the sequence of the light chain is set forth in SEQ ID NO:20.

9. The antibody of claim 5, wherein the sequence of the heavy chain is set forth in SEQ ID NO:21.

10. The antibody of claim 6, wherein the sequence of the light chain is set forth in SEQ ID NO:22.

11. A composition comprising the antibody of claim 1 and a suitable carrier.

12. The composition of claim 11, further comprising a second antibody.

13. A method of preventing or treating rabies in a subject which comprises administering to the subject a prophylactically or therapeutically effective amount of the antibody of claim 1.

14. A method of diagnosing rabies in a subject which comprises contacting a sample from the subject with the antibody of claim 1 under conditions permitting formation of a complex between the antibody and any rabies virus present in the sample and detecting any complex so formed.

15. A package comprising: 1) the composition of claim 11; and (2) a package insert providing instructions for use of the composition.

* * * * *

```
                         SEQUENCE LISTING

<160> NUMBER OF SEQ ID NOS: 42

<210> SEQ ID NO 1
<211> LENGTH: 524
<212> TYPE: PRT
<213> ORGANISM: Artificial Sequence
<220> FEATURE:
<223> OTHER INFORMATION: CVS-11 strain G protein

<400> SEQUENCE: 1

Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Pro Arg Thr Pro Cys
        195                 200                 205

Asp Ile Phe Thr Asn Ser Arg Gly Lys Arg Ala Ser Lys Gly Asn Lys
    210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
        275                 280                 285
```

```
His Leu Val Val Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
        355                 360                 365

Arg Cys His Pro His Val Asn Gly Val Phe Phe Asn Gly Ile Ile Leu
    370                 375                 380

Gly Pro Asp Gly His Val Leu Ile Pro Glu Met Gln Ser Ser Leu Leu
385                 390                 395                 400

Gln Gln His Met Glu Leu Leu Lys Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val Tyr Lys Gln Ile Ser Gly
        435                 440                 445

Val Asp Leu Gly Leu Pro Asn Trp Gly Lys Tyr Val Leu Met Thr Ala
    450                 455                 460

Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Arg Asn Val Ser Val Thr Ser Gln Ser Gly Lys Val Ile Pro Ser
            500                 505                 510

Trp Glu Ser Tyr Lys Ser Gly Gly Glu Ile Arg Leu
        515                 520

<210> SEQ ID NO 2
<211> LENGTH: 505
<212> TYPE: PRT
<213> ORGANISM: Artificial Sequence
<220> FEATURE:
<223> OTHER INFORMATION: CVS-11 strain G protein

<400> SEQUENCE: 2

Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
            20                  25                  30

Glu Gly Cys Thr Asn Leu Ser Glu Phe Ser Tyr Met Glu Leu Lys Val
        35                  40                  45

Gly Tyr Ile Ser Ala Ile Lys Val Asn Gly Phe Thr Cys Thr Gly Val
    50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Arg Thr Thr
        115                 120                 125
```

```
Lys Glu Ser Leu Ile Ile Ser Pro Ser Val Thr Asp Leu Asp Pro
            130                 135                 140

Tyr Asp Lys Ser Leu His Ser Arg Val Phe Pro Gly Gly Lys Cys Ser
145                 150                 155                 160

Gly Ile Thr Val Ser Ser Thr Tyr Cys Ser Thr Asn His Asp Tyr Thr
                165                 170                 175

Ile Trp Met Pro Glu Asn Pro Arg Pro Arg Thr Pro Cys Asp Ile Phe
            180                 185                 190

Thr Asn Ser Arg Gly Lys Arg Ala Ser Lys Gly Asn Lys Thr Cys Gly
        195                 200                 205

Phe Val Asp Glu Arg Gly Leu Tyr Lys Ser Leu Lys Gly Ala Cys Arg
    210                 215                 220

Leu Lys Leu Cys Gly Val Leu Gly Leu Arg Leu Met Asp Gly Thr Trp
225                 230                 235                 240

Val Ala Met Gln Thr Ser Asp Glu Thr Lys Trp Cys Pro Pro Asp Gln
                245                 250                 255

Leu Val Asn Leu His Asp Phe Arg Ser Asp Glu Ile Glu His Leu Val
            260                 265                 270

Val Glu Glu Leu Val Lys Lys Arg Glu Glu Cys Leu Asp Ala Leu Glu
        275                 280                 285

Ser Ile Met Thr Thr Lys Ser Val Ser Phe Arg Arg Leu Ser His Leu
    290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
                325                 330                 335

Glu Ile Ile Pro Ser Lys Gly Cys Leu Lys Val Gly Gly Arg Cys His
            340                 345                 350

Pro His Val Asn Gly Val Phe Phe Asn Gly Ile Ile Leu Gly Pro Asp
        355                 360                 365

Gly His Val Leu Ile Pro Glu Met Gln Ser Ser Leu Leu Gln Gln His
    370                 375                 380

Met Glu Leu Leu Lys Ser Ser Val Ile Pro Leu Met His Pro Leu Ala
385                 390                 395                 400

Asp Pro Ser Thr Val Phe Lys Glu Gly Asp Glu Ala Glu Asp Phe Val
                405                 410                 415

Glu Val His Leu Pro Asp Val Tyr Lys Gln Ile Ser Gly Val Asp Leu
            420                 425                 430

Gly Leu Pro Asn Trp Gly Lys Tyr Val Leu Met Thr Ala Gly Ala Met
        435                 440                 445

Ile Gly Leu Val Leu Ile Phe Ser Leu Met Thr Trp Cys Arg Arg Ala
    450                 455                 460

Asn Arg Pro Glu Ser Lys Gln Arg Ser Phe Gly Gly Thr Gly Arg Asn
465                 470                 475                 480

Val Ser Val Thr Ser Gln Ser Gly Lys Val Ile Pro Ser Trp Glu Ser
                485                 490                 495

Tyr Lys Ser Gly Gly Glu Ile Arg Leu
            500                 505
```

<210> SEQ ID NO 3
<211> LENGTH: 7
<212> TYPE: PRT
<213> ORGANISM: Artificial Sequence
<220> FEATURE:

<223> OTHER INFORMATION: Antibody 1 heavy chain CDR1

<400> SEQUENCE: 3

Arg Arg Arg Asp Tyr Trp Gly
1               5

<210> SEQ ID NO 4
<211> LENGTH: 16
<212> TYPE: PRT
<213> ORGANISM: Artificial Sequence
<220> FEATURE:
<223> OTHER INFORMATION: Antibody 1 heavy chain CDR2

<400> SEQUENCE: 4

Ser Phe Phe His Arg Gly Ser Thr Tyr Tyr Asn Pro Ser Leu Glu Ser
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Antibody 1 heavy chain CDR3

<400> SEQUENCE: 5

His Pro Ser Thr Pro Phe Ala Glu Tyr Leu Leu Leu Pro Asp Ala Phe
1               5                   10                  15

Asp Ser

<210> SEQ ID NO 6
<211> LENGTH: 11
<212> TYPE: PRT
<213> ORGANISM: Artificial Sequence
<220> FEATURE:
<223> OTHER INFORMATION: Antibody 1 light chain CDR1

<400> SEQUENCE: 6

Arg Ala Ser Gln Ser Val Arg Ser Ser Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Antibody 1 light chain CDR2

<400> SEQUENCE: 7

Gly Ala Ser Thr Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Antibody 1 light chain CDR3

<400> SEQUENCE: 8

Gln Gln Tyr Ser Asp Trp Pro Leu Thr
1               5

<210> SEQ ID NO 9
<211> LENGTH: 5
<212> TYPE: PRT
<213> ORGANISM: Artificial Sequence

```
<220> FEATURE:
<223> OTHER INFORMATION: Antibody 2 heavy chain CDR1

<400> SEQUENCE: 9

Ser Tyr Asp Ile Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Antibody 2 heavy chain CDR2

<400> SEQUENCE: 10

Trp Ile Ser Thr Tyr Lys Gly Asn Thr Asn Phe Ala Gln Lys Phe Gln
1               5                   10                  15

Asp

<210> SEQ ID NO 11
<211> LENGTH: 21
<212> TYPE: PRT
<213> ORGANISM: Artificial Sequence
<220> FEATURE:
<223> OTHER INFORMATION: Antibody 2 heavy chain CDR3

<400> SEQUENCE: 11

Ala Lys Ser His Pro Phe Tyr Asp Phe Trp Ser Ala Tyr Tyr Val Pro
1               5                   10                  15

Gly Ala Phe Asp Ile
            20

<210> SEQ ID NO 12
<211> LENGTH: 11
<212> TYPE: PRT
<213> ORGANISM: Artificial Sequence
<220> FEATURE:
<223> OTHER INFORMATION: Antibody 2 light chain CDR1

<400> SEQUENCE: 12

Gln Ala Ser Gln Asp Ile Ser Asn Tyr Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Antibody 2 light chain CDR2

<400> SEQUENCE: 13

Asp Ala Ser Asn Leu Glu Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Antibody 2 light chain CDR3

<400> SEQUENCE: 14

Gln Gln Tyr Asp Asn Leu Pro Leu Thr
1               5
```

<210> SEQ ID NO 15
<211> LENGTH: 129
<212> TYPE: PRT
<213> ORGANISM: Artificial Sequence
<220> FEATURE:
<223> OTHER INFORMATION: Antibody 1 heavy chain variable region

<400> SEQUENCE: 15

```
Glu Val Gln Leu Leu Gln Glu Ser Gly Pro Gly Leu Ala Lys Pro Ser
1               5                   10                  15

Glu Thr Leu Ser Leu Ile Cys Thr Val Ser Gly Gly Ser Ile Ser Arg
            20                  25                  30

Arg Arg Asp Tyr Trp Gly Trp Ile Arg Gln Pro Pro Gly Arg Gly Leu
        35                  40                  45

Glu Trp Ile Gly Ser Phe Phe His Arg Gly Ser Thr Tyr Tyr Asn Pro
    50                  55                  60

Ser Leu Glu Ser Arg Val Ser Ile Ser Val Asp Pro Ser Lys Asn Gln
65                  70                  75                  80

Phe Ser Leu His Leu Ser Ser Val Thr Val Ala Asp Thr Ala Val Tyr
                85                  90                  95

Tyr Cys Ala Arg His Pro Ser Thr Pro Phe Ala Glu Tyr Leu Leu Leu
            100                 105                 110

Pro Asp Ala Phe Asp Ser Trp Gly Gln Gly Thr Leu Val Thr Val Ser
        115                 120                 125

Ser
```

<210> SEQ ID NO 16
<211> LENGTH: 107
<212> TYPE: PRT
<213> ORGANISM: Artificial Sequence
<220> FEATURE:
<223> OTHER INFORMATION: Antibody 1 light chain variable region

<400> SEQUENCE: 16

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Ser
            20                  25                  30

Leu Ala Trp Tyr Gln Gln Arg Pro Gly Gln Ala Pro Arg Leu Leu Ile
        35                  40                  45

Ser Gly Ala Ser Thr Arg Ala Thr Asp Ile Pro Ala Arg Leu Ser Gly
    50                  55                  60

Ser Gly Ser Gly Thr Glu Phe Thr Leu Thr Val Ser Ser Leu Gln Ser
65                  70                  75                  80

Glu Asp Phe Ala Val Tyr Tyr Cys Gln Gln Tyr Ser Asp Trp Pro Leu
                85                  90                  95

Thr Phe Gly Gly Gly Thr Lys Val Glu Ile Lys
            100                 105
```

<210> SEQ ID NO 17
<211> LENGTH: 130
<212> TYPE: PRT
<213> ORGANISM: Artificial Sequence
<220> FEATURE:
<223> OTHER INFORMATION: Antibody 2 heavy chain variable region

<400> SEQUENCE: 17

```
Glu Val Gln Leu Val Glu Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Trp Ile Ser Thr Tyr Lys Gly Asn Thr Asn Phe Ala Gln Lys Phe
    50                  55                  60

Gln Asp Arg Val Thr Leu Thr Thr Asp Thr Ser Thr Thr Thr Ala Tyr
65                  70                  75                  80

Met Glu Leu Arg Ser Leu Thr Ser Asp Asp Thr Ala Val Tyr Tyr Cys
                85                  90                  95

Ala Arg Ala Lys Ser His Pro Phe Tyr Asp Phe Trp Ser Ala Tyr Tyr
            100                 105                 110

Val Pro Gly Ala Phe Asp Ile Trp Gly Gln Gly Thr Val Val Thr Val
        115                 120                 125

Ser Ser
    130

<210> SEQ ID NO 18
<211> LENGTH: 107
<212> TYPE: PRT
<213> ORGANISM: Artificial Sequence
<220> FEATURE:
<223> OTHER INFORMATION: Antibody 2 light chain variable region

<400> SEQUENCE: 18

Glu Leu Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Pro Gly Thr Lys Val Asp Ile Lys
            100                 105

<210> SEQ ID NO 19
<211> LENGTH: 459
<212> TYPE: PRT
<213> ORGANISM: Artificial Sequence
<220> FEATURE:
<223> OTHER INFORMATION: Antibody 1 heavy chain

<400> SEQUENCE: 19

Glu Val Gln Leu Leu Gln Glu Ser Gly Pro Gly Leu Ala Lys Pro Ser
1               5                   10                  15

Glu Thr Leu Ser Leu Ile Cys Thr Val Ser Gly Gly Ser Ile Ser Arg
            20                  25                  30

Arg Arg Asp Tyr Trp Gly Trp Ile Arg Gln Pro Pro Gly Arg Gly Leu
        35                  40                  45

Glu Trp Ile Gly Ser Phe Phe His Arg Gly Ser Thr Tyr Tyr Asn Pro
    50                  55                  60

Ser Leu Glu Ser Arg Val Ser Ile Ser Val Asp Pro Ser Lys Asn Gln
65                  70                  75                  80
```

```
        Phe Ser Leu His Leu Ser Ser Val Thr Val Ala Asp Thr Ala Val Tyr
                    85                  90                  95

Tyr Cys Ala Arg His Pro Ser Thr Pro Phe Ala Glu Tyr Leu Leu Leu
                    100                 105                 110

Pro Asp Ala Phe Asp Ser Trp Gly Gln Gly Thr Leu Val Thr Val Ser
                    115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
        145                 150                 155                 160

Tyr Phe Pro Glu Pro Val Thr Val Ser Trp Asn Ser Gly Ala Leu Thr
                    165                 170                 175

Ser Gly Val His Thr Phe Pro Ala Val Leu Gln Ser Ser Gly Leu Tyr
                    180                 185                 190

Ser Leu Ser Ser Val Val Thr Val Pro Ser Ser Ser Leu Gly Thr Gln
                    195                 200                 205

Thr Tyr Ile Cys Asn Val Asn His Lys Pro Ser Asn Thr Lys Val Asp
        210                 215                 220

Lys Lys Val Glu Pro Lys Ser Cys Asp Lys Thr His Thr Cys Pro Pro
        225                 230                 235                 240

Cys Pro Ala Pro Glu Leu Leu Gly Gly Pro Ser Val Phe Leu Phe Pro
                    245                 250                 255

Pro Lys Pro Lys Asp Thr Leu Met Ile Ser Arg Thr Pro Glu Val Thr
                    260                 265                 270

Cys Val Val Val Asp Val Ser His Glu Asp Pro Glu Val Lys Phe Asn
                    275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
        305                 310                 315                 320

Leu His Gln Asp Trp Leu Asn Gly Lys Glu Tyr Lys Cys Lys Val Ser
                    325                 330                 335

Asn Lys Ala Leu Pro Ala Pro Ile Glu Lys Thr Ile Ser Lys Ala Lys
                    340                 345                 350

Gly Gln Pro Arg Glu Pro Gln Val Tyr Thr Leu Pro Pro Ser Arg Asp
                    355                 360                 365

Glu Leu Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
        385                 390                 395                 400

Asn Asn Tyr Lys Thr Thr Pro Pro Val Leu Asp Ser Asp Gly Ser Phe
                    405                 410                 415

Phe Leu Tyr Ser Lys Leu Thr Val Asp Lys Ser Arg Trp Gln Gln Gly
                    420                 425                 430

Asn Val Phe Ser Cys Ser Val Met His Glu Ala Leu His Asn His Tyr
                    435                 440                 445

Thr Gln Lys Ser Leu Ser Leu Ser Pro Gly Lys
            450                 455

<210> SEQ ID NO 20
<211> LENGTH: 214
<212> TYPE: PRT
<213> ORGANISM: Artificial Sequence
<220> FEATURE:
```

<223> OTHER INFORMATION: Antibody 1 light chain

<400> SEQUENCE: 20

```
Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Ser
            20                  25                  30

Leu Ala Trp Tyr Gln Gln Arg Pro Gly Gln Ala Pro Arg Leu Leu Ile
        35                  40                  45

Ser Gly Ala Ser Thr Arg Ala Thr Asp Ile Pro Ala Arg Leu Ser Gly
    50                  55                  60

Ser Gly Ser Gly Thr Glu Phe Thr Leu Thr Val Ser Ser Leu Gln Ser
65                  70                  75                  80

Glu Asp Phe Ala Val Tyr Tyr Cys Gln Gln Tyr Ser Asp Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 460
<212> TYPE: PRT
<213> ORGANISM: Artificial Sequence
<220> FEATURE:
<223> OTHER INFORMATION: Antibody 2 heavy chain

<400> SEQUENCE: 21

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Trp Ile Ser Thr Tyr Lys Gly Asn Thr Asn Phe Ala Gln Lys Phe
    50                  55                  60

Gln Asp Arg Val Thr Leu Thr Thr Asp Thr Ser Thr Thr Thr Ala Tyr
65                  70                  75                  80

Met Glu Leu Arg Ser Leu Thr Ser Asp Asp Thr Ala Val Tyr Tyr Cys
                85                  90                  95

Ala Arg Ala Lys Ser His Pro Phe Tyr Asp Phe Trp Ser Ala Tyr Tyr
            100                 105                 110

Val Pro Gly Ala Phe Asp Ile Trp Gly Gln Gly Thr Val Val Thr Val
        115                 120                 125
```

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
450                 455                 460

<210> SEQ ID NO 22
<211> LENGTH: 214
<212> TYPE: PRT
<213> ORGANISM: Artificial Sequence
<220> FEATURE:
<223> OTHER INFORMATION: Antibody 2 light chain

<400> SEQUENCE: 22

Glu Leu Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

-continued

```
Leu Asn Trp Tyr Gln Gln Lys Pro Gly Lys Ala Pro Lys Leu Leu Ile
             35                  40                  45
Tyr Asp Ala Ser Asn Leu Glu Thr Gly Val Pro Ser Arg Phe Ser Gly
 50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Tyr Asp Asn Leu Pro Leu
                 85                  90                  95
Thr Phe Gly Pro Gly Thr Lys Val Asp Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 23
<211> LENGTH: 21
<212> TYPE: DNA
<213> ORGANISM: Artificial Sequence
<220> FEATURE:
<223> OTHER INFORMATION: Antibody 1 heavy chain CDR1

<400> SEQUENCE: 23
cggcggagag actactgggg c                                             21

<210> SEQ ID NO 24
<211> LENGTH: 48
<212> TYPE: DNA
<213> ORGANISM: Artificial Sequence
<220> FEATURE:
<223> OTHER INFORMATION: Antibody 1 heavy chain CDR2

<400> SEQUENCE: 24
agcttcttcc accggggcag cacctactac aaccccagcc tggaaagc                48

<210> SEQ ID NO 25
<211> LENGTH: 54
<212> TYPE: DNA
<213> ORGANISM: Artificial Sequence
<220> FEATURE:
<223> OTHER INFORMATION: Antibody 1 heavy chain CDR3

<400> SEQUENCE: 25
caccccagca ccccttcgc cgagtacctg ctgctgcccg acgccttcga tagc          54

<210> SEQ ID NO 26
<211> LENGTH: 33
<212> TYPE: DNA
<213> ORGANISM: Artificial Sequence
<220> FEATURE:
```

<223> OTHER INFORMATION: Antibody 1 light chain CDR1

<400> SEQUENCE: 26
agagccagcc agagcgtgcg gagcagcctg gcc                         33

<210> SEQ ID NO 27
<211> LENGTH: 21
<212> TYPE: DNA
<213> ORGANISM: Artificial Sequence
<220> FEATURE:
<223> OTHER INFORMATION: Antibody 1 light chain CDR2

<400> SEQUENCE: 27
ggcgccagca ccagagccac c                                      21

<210> SEQ ID NO 28
<211> LENGTH: 27
<212> TYPE: DNA
<213> ORGANISM: Artificial Sequence
<220> FEATURE:
<223> OTHER INFORMATION: Antibody 1 light chain CDR3

<400> SEQUENCE: 28
cagcagtaca gcgactggcc cctgacc                                27

<210> SEQ ID NO 29
<211> LENGTH: 15
<212> TYPE: DNA
<213> ORGANISM: Artificial Sequence
<220> FEATURE:
<223> OTHER INFORMATION: Antibody 2 heavy chain CDR1

<400> SEQUENCE: 29
agctatgata tcagc                                             15

<210> SEQ ID NO 30
<211> LENGTH: 51
<212> TYPE: DNA
<213> ORGANISM: Artificial Sequence
<220> FEATURE:
<223> OTHER INFORMATION: Antibody 2 heavy chain CDR2

<400> SEQUENCE: 30
tggatcagca cttacaaggg taacacaaac tttgcacaaa agttccagga c      51

<210> SEQ ID NO 31
<211> LENGTH: 63
<212> TYPE: DNA
<213> ORGANISM: Artificial Sequence
<220> FEATURE:
<223> OTHER INFORMATION: Antibody 2 heavy chain CDR3

<400> SEQUENCE: 31
gccaaatccc accgttttta cgatttttgg agtgcttact atgtccccgg tgcttttgat 60
atc                                                          63

<210> SEQ ID NO 32
<211> LENGTH: 33
<212> TYPE: DNA
<213> ORGANISM: Artificial Sequence
<220> FEATURE:
<223> OTHER INFORMATION: Antibody 2 light chain CDR1

<400> SEQUENCE: 32
caggcgagtc aggacattag caactattta aat                         33

<210> SEQ ID NO 33
<211> LENGTH: 21
<212> TYPE: DNA
<213> ORGANISM: Artificial Sequence
<220> FEATURE:
<223> OTHER INFORMATION: Antibody 2 light chain CDR2

<400> SEQUENCE: 33
gatgcatcca atttggaaac a                                           21

<210> SEQ ID NO 34
<211> LENGTH: 27
<212> TYPE: DNA
<213> ORGANISM: Artificial Sequence
<220> FEATURE:
<223> OTHER INFORMATION: Antibody 2 light chain CDR3

<400> SEQUENCE: 34
caacagtatg ataatctccc ccttact                                     27

<210> SEQ ID NO 35
<211> LENGTH: 387
<212> TYPE: DNA
<213> ORGANISM: Artificial Sequence
<220> FEATURE:
<223> OTHER INFORMATION: Antibody 1 heavy chain variable region

<400> SEQUENCE: 35
gaagtgcagc tgctgcagga aagcggccct ggcctggcca agcccagcga gacactgagc    60
ctgatctgca ccgtgtccgg cggcagcatc agccggcgga gagactactg gggctggatc   120
agacagcccc ctggcagagg cctggaatgg atcggcagct tcttccaccg gggcagcacc   180
tactacaacc ccagcctgga aagccgggtg tccatcagcg tggaccccag caagaaccag   240
ttcagcctgc acctgagcag cgtgaccgtg gccgacaccg ccgtgtacta ctgcgccaga   300
caccccagca cccccttcgc cgagtacctg ctgctgcccg acgccttcga tgctggggc   360 cagggcaccc tggtgacagt gtccagc                                       387

<210> SEQ ID NO 36
<211> LENGTH: 321
<212> TYPE: DNA
<213> ORGANISM: Artificial Sequence
<220> FEATURE:
<223> OTHER INFORMATION: Antibody 1 light chain variable region

<400> SEQUENCE: 36
gacatcgtga tgacccagag ccccgccacc ctgagcgtgt ccccaggcga gagagccacc    60
ctgtcctgca gagccagcca gagcgtgcgg agcagcctgg cctggtatca gcagaggcca   120
ggccaggccc ccagactgct gatcagcggc gccagcacca gagccaccga catccctgcc   180
agactgagcg gcagcggctc cggcaccgag ttcaccctga cagtgtccag cctgcagagc   240
gaggacttcg ccgtgtacta ctgccagcag tacagcgact ggcccctgac cttcggcgga   300
ggcaccaagg tggaaatcaa g                                             321

<210> SEQ ID NO 37
<211> LENGTH: 390
<212> TYPE: DNA
<213> ORGANISM: Artificial Sequence
<220> FEATURE:
<223> OTHER INFORMATION: Antibody 2 heavy chain variable region

<400> SEQUENCE: 37

| gaggtgcagc tggtggagtc tgagctgag gtgaagaagc ctggggcctc agtgaaggtc | 60 |
| tcctgcaagg cttctggtta cacctttacc agctatgata tcagctgggt gcgacaggcc | 120 |
| cctggacaag gcttgagtg gatgggatgg atcagcactt acaagggtaa cacaaacttt | 180 |
| gcacaaaagt tccaggacag agtcacccttt accacagaca catccacgac cacagcctac | 240 |
| atggagctga ggagcctgac atctgacgac acggccgtgt attactgtgc gagagccaaa | 300 |
| tcccacccgt tttacgattt ttggagtgct actatgtcc ccggtgcttt tgatatctgg | 360 |
| ggccaaggga cagtggtcac cgtctcttca | 390 |

<210> SEQ ID NO 38
<211> LENGTH: 321
<212> TYPE: DNA
<213> ORGANISM: Artificial Sequence
<220> FEATURE:
<223> OTHER INFORMATION: Antibody 2 light chain variable region

<400> SEQUENCE: 38

| gagctcgtga tgacgcagtc tccatcctcc ctgtctgcat ctgtaggaga cagagtcacc | 60 |
| atcacttgcc aggcgagtca ggacattagc aactatttaa attggtatca gcagaaacca | 120 |
| gggaaagccc ctaagctcct gatctacgat gcatccaatt tggaaacagg gtcccatca | 180 |
| aggttcagtg gaagtggatc tgggacagat tttactttca ccatcagcag cctgcagcct | 240 |
| gaagatattg caacatatta ctgtcaacag tatgataatc tccccttac tttcggccct | 300 |
| gggaccaaag tggatatcaa a | 321 |

<210> SEQ ID NO 39
<211> LENGTH: 1380
<212> TYPE: DNA
<213> ORGANISM: Artificial Sequence
<220> FEATURE:
<223> OTHER INFORMATION: Antibody 1 heavy chain

<400> SEQUENCE: 39

| gaagtgcagc tgctgcagga aagcggccct ggcctggcca agcccagcga gacactgagc | 60 |
| ctgatctgca ccgtgtccgg cggcagcatc agccggcgga gagactactg ggctggatc | 120 |
| agacagcccc ctggcagagg cctggaatgg atcggcagct tcttccaccg gggcagcacc | 180 |
| tactacaacc ccagcctgga aagccgggtg tccatcagcg tggaccccag caagaaccag | 240 |
| ttcagcctgc acctgagcag cgtgaccgtg ccgacaccg ccgtgtacta ctgcgccaga | 300 |
| caccccagca ccccccttcgc cgagtacctg ctgctgcccg acgccttcga tagctggggc | 360 |
| cagggcaccc tggtgacagt gtccagcgcc agcaccaagg gcccagcgt gttccctctg | 420 |
| gcccccagca gcaagagcac atctggcgga acagccgccc tgggctgcct ggtgaaagac | 480 |
| tacttccccg aaccggtgac ggtgtcgtgg aactcaggcg ccctgaccag cggcgtgcac | 540 |
| accttcccgg ctgtcctaca gtcctcagga ctctactccc tcagcagcgt ggtgaccgtg | 600 |
| ccctccagca gcttgggcac ccagacctac atctgcaacg tgaatcacaa gcccagcaac | 660 |
| accaaggtgg acaagaaagt tgagcccaaa tcttgtgaca aaactcacac atgcccaccg | 720 |
| tgcccagcac ctgaactcct ggggggaccg tcagtcttcc tcttcccccc aaaacccaag | 780 |
| gacaccctca tgatctcccg gacccctgag gtcacatgcg tggtggtgga cgtgagccac | 840 |
| gaagaccctg aggtcaagtt caactggtac gtggacggcg tggaggtgca taatgccaag | 900 |
| acaaagccgc gggaggagca gtacaacagc acgtaccggg tggtcagcgt cctcaccgtc | 960 |

```
ctgcaccagg actggctgaa tggcaaggag tacaagtgca aggtctccaa caaagccctc    1020
ccagccccca tcgagaaaac catctccaaa gccaagggc agccccgaga ccacaggtg     1080 tacaccctgc ccccatcccg ggatgagctg accaagaacc aggtcagcct gacctgcctg    1140
gtcaaaggct tctatcccag cgacatcgcc gtggagtggg agagcaatgg gcagccggag    1200
aacaactaca agaccacgcc tcccgtgctg gactccgacg gctccttctt cctctacagc    1260
aagctcaccg tggacaagag caggtggcag caggggaacg tcttctcatg ctccgtgatg    1320
catgaggctc tgcacaacca ctacacgcag aagagcctct ccctgtctcc gggtaaatga    1380
```

<210> SEQ ID NO 40
<211> LENGTH: 645
<212> TYPE: DNA
<213> ORGANISM: Artificial Sequence
<220> FEATURE:
<223> OTHER INFORMATION: Antibody 1 light chain

<400> SEQUENCE: 40

```
gacatcgtga tgacccagag ccccgccacc ctgagcgtgt ccccaggcga gagagccacc     60
ctgtcctgca gagccagcca gagcgtgcgg agcagcctgg cctggtatca gcagaggcca    120
ggccaggccc ccagactgct gatcagcggc gccagcacca gagccaccga catccctgcc    180
agactgagcg gcagcggctc cggcaccgag ttcaccctga cagtgtccag cctgcagagc    240
gaggacttcg ccgtgtacta ctgccagcag tacagcgact ggcccctgac cttcggcgga    300
ggcaccaagg tggaaatcaa gcggaccgtg gccgctccca gcgtgttcat cttcccaccc    360
agcgacgagc agctgaagtc cggcacagcc agcgtggtgt gcctgctgaa caacttctac    420
ccccgcgagg ccaaggtgca gtggaaggtg gacaacgccc tgcagtccgg caactcccag    480
gaaagcgtga ccgagcagga cagcaaggac tccacctaca gcctgagcag cacccctgacc    540 ctgagcaagg ccgactacga aaagcacaag gtgtacgcct gcgaagtgac ccaccagggc    600
ctgtccagcc ccgtgaccaa gagcttcaac cggggcgagt gctga                    645
```

<210> SEQ ID NO 41
<211> LENGTH: 1383
<212> TYPE: DNA
<213> ORGANISM: Artificial Sequence
<220> FEATURE:
<223> OTHER INFORMATION: Antibody 2 heavy chain

<400> SEQUENCE: 41

```
gaggtgcagc tggtggagtc tggagctgag gtgaagaagc ctggggcctc agtgaaggtc     60
tcctgcaagg cttctggtta cacctttacc agctatgata tcagctgggt gcgacaggcc    120
cctggacaag gcttgagtg gatgggatgg atcagcactt acaagggtaa cacaaacttt    180
gcacaaaagt tccaggacag agtcacccctt accacagaca catccacgac cacagcctac    240
atggagctga ggagcctgac atctgacgac acggccgtgt attactgtgc gagagccaaa    300
tcccacccgt tttacgattt ttggagtgct actatgtcc ccggtgcttt tgatatctgg     360
ggccaaggga cagtggtcac cgtctcttca gcttccacca agggcccatc ggtcttcccc    420
ctggcaccct cctccaagag cacctctggg ggcacagcag ccctgggctg cctggtcaag    480
gactacttcc ccgaaccggt gacggtgtcg tggaactcag gcgccctgac cagcggcgtg    540
cacaccttcc cggctgtcct acagtcctca ggactctact ccctcagcag cgtggtgacc    600
gtgccctcca gcagcttggg cacccagacc tacatctgca acgtgaatca caagcccagc    660
```

```
aacaccaagg tggacaagaa agttgagccc aaatcttgtg acaaaactca cacatgccca    720
ccgtgcccag cacctgaact cctgggggga ccgtcagtct tcctcttccc cccaaaaccc    780
aaggacaccc tcatgatctc ccggacccct gaggtcacat gcgtggtggt ggacgtgagc    840
cacgaagacc ctgaggtcaa gttcaactgg tacgtggacg gcgtggaggt gcataatgcc    900
aagacaaagc cgcgggagga gcagtacaac agcacgtacc gtgtggtcag cgtcctcacc    960
gtcctgcacc aggactggct gaatggcaag gagtacaagt gcaaggtctc caacaaagcc   1020
ctcccagccc ccatcgagaa aaccatctcc aaagccaaag gcagccccg agaaccacag    1080 gtgtacaccc tgcccccatc ccgggaggag atgaccaaga accaggtcag cctgacctgc   1140
ctggtcaaag gcttctatcc cagcgacatc gccgtggagt gggagagcaa tgggcagccg   1200
gagaacaact acaagaccac gcctcccgtg ctggactccg acggctcctt cttcctctac   1260
agcaagctca ccgtggacaa gagcaggtgg cagcagggga acgtcttctc atgctccgtg   1320
atgcatgagg ctctgcacaa ccactacaca cagaagagcc tctccctgtc tccgggtaaa   1380
tga                                                                 1383

<210> SEQ ID NO 42
<211> LENGTH: 645
<212> TYPE: DNA
<213> ORGANISM: Artificial Sequence
<220> FEATURE:
<223> OTHER INFORMATION: Antibody 2 light chain

<400> SEQUENCE: 42
gagctcgtga tgacgcagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgataatc tccccttac tttcggccct    300 gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```